(12) United States Patent
Toth

(10) Patent No.: US 12,295,646 B2
(45) Date of Patent: *May 13, 2025

(54) SMART TORQUER AND METHODS OF USING THE SAME

(71) Applicant: Autonomix Medical, Inc., Ivyland, PA (US)

(72) Inventor: Landy Toth, Ivyland, PA (US)

(73) Assignee: Autonomix Medical, Inc., Ivyland, PA (US)

( * ) Notice: Subject to any disclaimer, the term of this patent is extended or adjusted under 35 U.S.C. 154(b) by 1196 days.

This patent is subject to a terminal disclaimer.

(21) Appl. No.: 16/951,317

(22) Filed: Nov. 18, 2020

(65) Prior Publication Data

US 2021/0077182 A1 Mar. 18, 2021

Related U.S. Application Data

(63) Continuation-in-part of application No. 15/272,045, filed on Sep. 21, 2016, now Pat. No. 10,874,830.
(Continued)

(51) Int. Cl.
*A61B 5/00* (2006.01)
*A61B 18/14* (2006.01)
(Continued)

(52) U.S. Cl.
CPC ......... *A61B 18/1492* (2013.01); *G16H 40/67* (2018.01); *A61B 2018/00077* (2013.01);
(Continued)

(58) Field of Classification Search
CPC ... A61B 5/042; A61B 5/6852; A61B 18/1492;
A61B 34/70; A61B 2018/00077; A61B 2018/00083; A61B 2018/00273; A61B 2018/00351; A61B 2018/00571; A61B 2560/0214; A61B 2560/0285; A61M 25/0113; A61M 25/0136; A61M 25/09041; A61M 2025/0166; A61M 2025/09116;
(Continued)

(56) References Cited

U.S. PATENT DOCUMENTS 4,954,149 A 9/1990 Fullemann
5,222,164 A * 6/1993 Bass, Sr. ............ H01R 13/6683
439/488
(Continued)

FOREIGN PATENT DOCUMENTS

DE 102012104961 A1 12/2013
EP 0466424 A1 1/1992
WO WO-2011143621 A1 * 11/2011 ........ A61M 25/0097

*Primary Examiner* — May A Abouelela
(74) *Attorney, Agent, or Firm* — Ryan, Mason & Lewis, LLP

(57) ABSTRACT

Smart torquers are provided. Aspects of the smart torquers include: an engager for releasably engaging an elongated intravascular device; a communications module; a contact associated with the engager and configured to communicatively contact an elongated intravascular device engaged by the engager with the communications module; and a manipulator configured to allow a user to torque an elongated intravascular device engaged by the engager. Aspects of the invention further include methods of using the smart torquers, as well as systems and kits employed in such methods.

21 Claims, 8 Drawing Sheets

Related U.S. Application Data

(60) Provisional application No. 62/237,328, filed on Oct. 5, 2015.

(51) Int. Cl.
*G16H 40/67* (2018.01)
*A61B 18/00* (2006.01)

(52) U.S. Cl.
CPC ............... *A61B 2018/00083* (2013.01); *A61B 2018/00273* (2013.01); *A61B 2018/00351* (2013.01); *A61B 2018/00571* (2013.01); *A61B 2560/0214* (2013.01); *A61B 2560/0285* (2013.01)

(58) Field of Classification Search
CPC .......... A61M 2205/3592; G16H 40/67; G16H 20/40; G16H 40/63; G16H 50/20
See application file for complete search history.

(56) References Cited

U.S. PATENT DOCUMENTS

| | | | |
|---|---|---|---|
| 5,325,868 A | 7/1994 | Kimmelstiel | |
| 5,568,815 A | 10/1996 | Raynes et al. | |
| 5,643,255 A | 7/1997 | Organ | |
| 5,857,997 A | 1/1999 | Cimino et al. | |
| 6,030,349 A | 2/2000 | Wilson et al. | |
| 6,971,907 B1 * | 12/2005 | Stroud | H01R 13/6641 439/490 |
| 7,144,378 B2 | 12/2006 | Arnott | |
| 7,724,148 B2 | 5/2010 | Samuelsson et al. | |
| 8,403,869 B2 | 3/2013 | Kasasbeh | |
| 9,522,048 B1 * | 12/2016 | Schmit | A61B 5/304 |
| 2002/0161421 A1 | 10/2002 | Lee et al. | |
| 2002/0177772 A1 | 11/2002 | Altman et al. | |
| 2005/0277851 A1 | 12/2005 | Whittaker et al. | |
| 2007/0219467 A1 | 9/2007 | Clark et al. | |
| 2009/0270941 A1 | 10/2009 | Mokelke et al. | |
| 2010/0204613 A1 | 8/2010 | Rollins et al. | |
| 2011/0079423 A1 | 4/2011 | Zhao et al. | |
| 2011/0151698 A1 * | 6/2011 | Boyd | H01R 13/514 439/246 |
| 2012/0296262 A1 | 11/2012 | Ogata et al. | |
| 2013/0109980 A1 | 5/2013 | Teo | |
| 2013/0331676 A1 | 12/2013 | Morgan et al. | |
| 2014/0206959 A1 | 7/2014 | Samuelsson et al. | |
| 2015/0105654 A1 | 4/2015 | Meyer | |
| 2015/0148877 A1 | 5/2015 | Thakkar et al. | |
| 2015/0182188 A1 | 7/2015 | Corl | |
| 2016/0051323 A1 * | 2/2016 | Stigall | A61B 17/22 600/407 |
| 2016/0351292 A1 | 12/2016 | Toth et al. | |

* cited by examiner

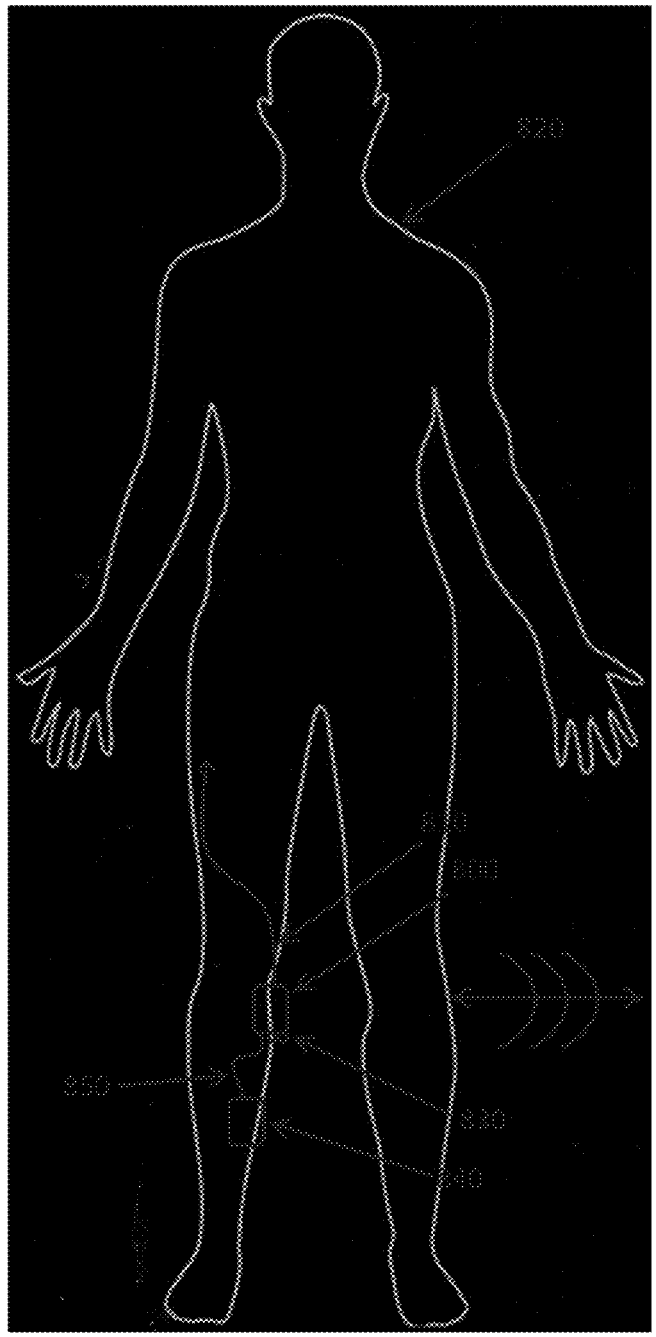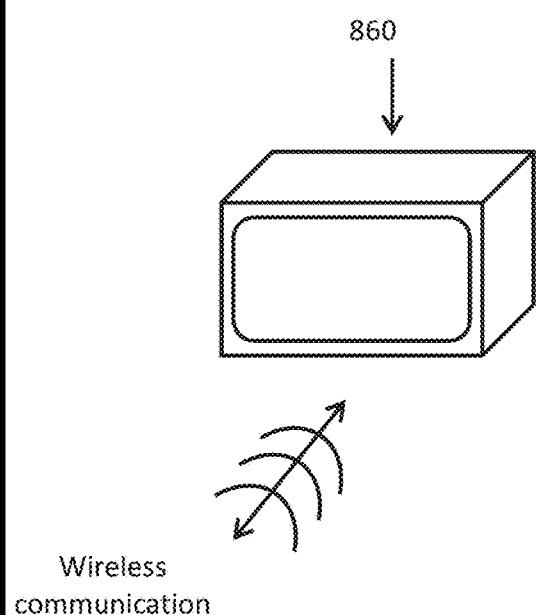
FIG. 8
860
Wireless communication

SMART TORQUER AND METHODS OF USING THE SAME

CROSS-REFERENCE TO RELATED APPLICATIONS

This application is a continuation of U.S. patent application Ser. No. 15/272,045 filed Sep. 21, 2016, now issued as U.S. Pat. No. 10,874,830, which application, pursuant Pursuant to 35 U.S.C. § 119 (e), this application claims priority to the filing date of the U.S. Provisional Patent Application Ser. No. 62/237,328, filed Oct. 5, 2015, the disclosures of which are incorporated herein by reference.

INTRODUCTION

Minimally invasive surgery holds many advantages over more invasive surgical techniques including decreased trauma and scarring for patients, decreased operative blood loss, shorter healing time, decreased risk of infection and decreased length of hospital stays. However, minimally invasive procedures are complicated by several factors, including the difficulty of reaching the operative site with surgical tools and maneuvering those tools within the body. This can be even more complicated in operations where the entry site of the tools is far from the operative site. For example, an endovascular surgery may have its entry site at the femoral artery of the thigh and its operative site at the carotid artery located in the neck.

A common method of operation in minimally invasive surgery is to first thread a guidewire to the operative site, and then thread various tools over the guidewire to reach said site. Success of this procedure relies on sufficient flexibility and maneuverability of the guidewire. The surgeon must be able to navigate and traverse the many twists and turns of the circulatory (or other) system to reach the operative site. However, guidewires are relatively fine and difficult to grip between a surgeon's fingers.

As such, a device called a wire manipulator, torque device or simply "torquer" is often affixed to the wire and allows the surgeon to more precisely control movement of the wire and to negotiate the various turns and branches of the cardiovascular system. That is, the torquer allows the surgeon to apply torque so as to manipulate the distal end of the guide wire. In addition to its use in the field of interventional cardiology, such torquers may also be used in vascular procedures, neurosurgical procedures, interventional radiological procedures.

Generally, conventional guidewire torquers are configured to be attached from the proximal end of the guidewire. Specifically, most conventional guidewire torquers are threaded onto the proximal end of the guidewire, and then advanced along the wire until a suitable location is reached. Such a guidewire torquer is then clamped or secured to the guidewire at the suitable location.

SUMMARY

Smart torquers are provided. Aspects of the smart torquers include: an engager for releasably engaging an elongated intravascular device; a communications module; a contact associated with the engager and configured to communicatively contact an elongated intravascular device engaged by the engager with the communications module; and a manipulator configured to allow a user to torque an elongated intravascular device engaged by the engager. Aspects of the invention further include methods of using the smart torquers, as well as systems and kits employed in such methods.

BRIEF DESCRIPTION OF THE FIGURES

FIG. 8 provides a view of a smart torquer/smart guidewire system being employed with a patient, in accordance with an embodiment of the invention.

DETAILED DESCRIPTION

Figure 1:
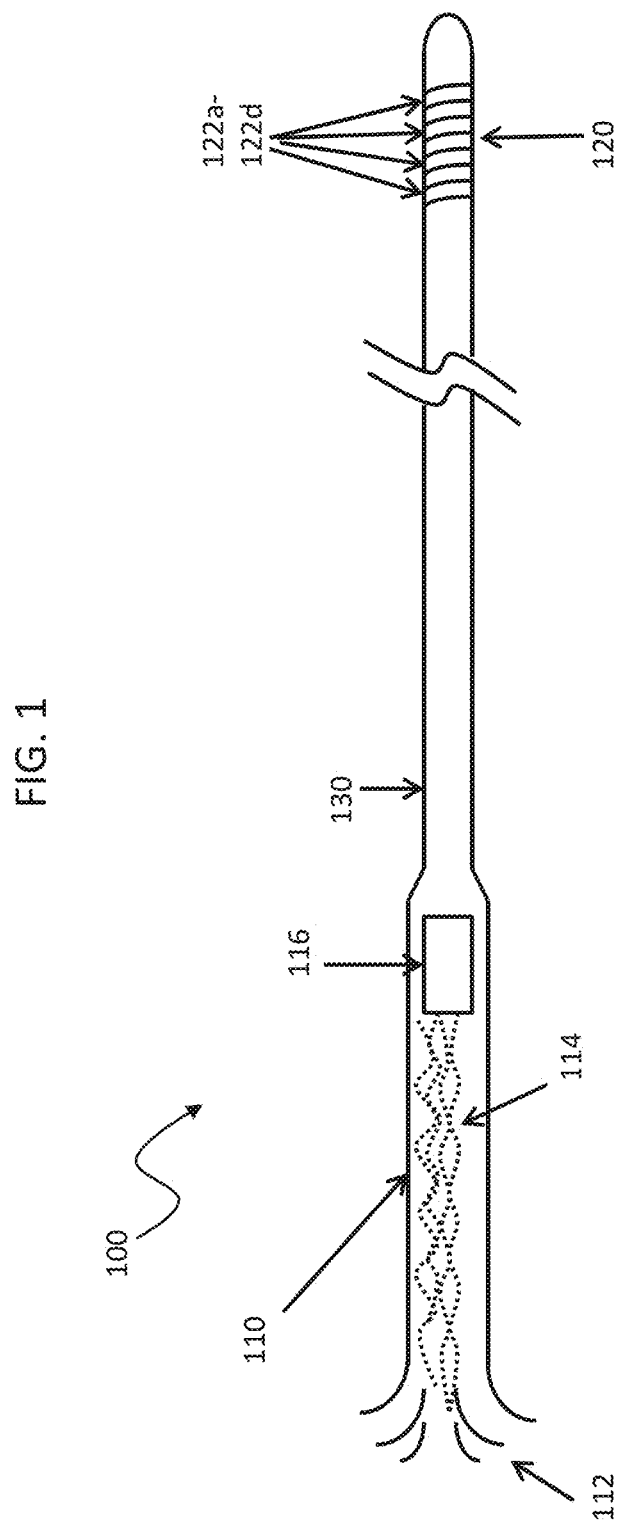
FIG. 1 provides a schematic illustration of an elongated intravascular device having an effector made up of a plurality of microfingers at a distal end, which may be operated by a smart torquer according to an embodiment of the invention.

Smart torquers are provided. Aspects of the smart torquers include: an engager for releasably engaging an elongated intravascular device; a communications module; a contact associated with the engager and configured to communicatively contact an elongated intravascular device engaged by the engager with the communications module; and a manipulator configured to allow a user to torque an elongated intravascular device engaged by the engager. Aspects of the invention further include methods of using the smart torquers, as well as systems and kits employed in such methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing various aspects of the invention, smart torquers and systems that include the same will be described first in greater detail, followed by a review of embodiments of methods of using the smart torquers and systems, as well as kits that may include smart torquers.

Smart Torquers

As summarized above, aspects of the invention include smart torquers. The phrase "smart torquer" refers to a device (which may also be referred to as a torque device or simply "torquer") that is configured to engage an elongated intravascular device, such as a guide wire or catheter, and allow an operator to more precisely control movement of the device and distal end thereof, e.g., as it moves through a cardiovascular system. As the torquers of the invention are smart, they are configured to receive data from a source, e.g., to receive data initially obtained from an elongated intravascular device operably engaged by the smart torquer, then output the received data, e.g., to a user, a second device, etc., where the smart torquer may or may not be further configured to process the received data in some manner prior to outputting the data. This "smart" ability to receive and output data, e.g., with or without processing, may be implemented in a variety of different hardware and/or software components, e.g., as described in greater detail below.

Smart torquers of embodiments of the invention are configured to apply torque to an elongated intravascular device operably engaged by the smart torquer. The phrase "elongated intravascular device" as used herein refers to an elongated structure having a proximal region and a distal region, which structure is elongated and configured to be movably positioned in a mammalian vascular system, such as a mammalian cardiovascular system, e.g., a human cardiovascular system. As the elongated intravascular device is elongated, the elongated intravascular device has an elongated structure in which the length (extending from the proximal end of the proximal region to the distal end of the distal region) is longer than the longest cross-sectional dimension of the structure. While the ratio of length to longest cross-sectional dimension may vary, in some instances this ratio ranges from 20:1 to 50,000:1, such as 750:1 to 7,500:1, and including 1,000:1 to 5,000:1. In some instances, the elongated intravascular device has a length ranging from 5 to 3,000 mm, such as 50 to 2,000 mm and including 750 to 1750 mm. As the elongated intravascular device is configured to be movably positioned in a vascular system, the device has a longest cross-sectional dimension that provides for such movement. While the longest cross-sectional dimension may vary among different devices, in some instances the device has a longest cross-sectional dimension (e.g., diameter in those embodiments where the conductor is cylindrical in shape) ranging from 0.025 to 20.0 mm, such as 0.10 to 5.0 mm and including 0.10 to 1.0 mm. The cross-sectional shape of the conductor may vary, where examples of cross-sectional shapes that may be found in the conductors include, but are not limited to: rectilinear shapes, e.g., rectangular, square, triangular, trapezoidal, etc., curvilinear shapes, e.g., circular, oval, etc.; as well as irregular shapes. In some instances, the structure of the elongated conductor has a circular cross section, such that the structure is cylindrical. Examples of types of elongated intravascular devices for which the smart torquers of the invention may be configured to manipulate include, but are not limited to: guidewires, catheters, etc. The term "guidewire" is employed in its conventional sense to refer to a device, such as a wire, used to enter tight spaces, e.g., obstructed valves or channels, within the body, or to assist in inserting, positioning, and moving a catheter. The term "catheter" is employed in its conventional sense to refer to a tubular, flexible instrument, passed through body channels for withdrawal of fluids from (or introduction of fluids into) a body cavity.

In some embodiments, the elongated intravascular devices are elongated conductors that are configured to convey different entities, e.g., electrical current, charge, light, fluids, including gasses and liquids, etc. In some instances, the conductors are configured to convey electric current, such that they are electrical conductors. In some instances, the conductors are meant to convey light, such that they are optical fibers. Elongated conductors of the invention may include two or more insulated conducting members that are in fixed relative position along at least a portion of the elongated structure and extend from the proximal region to the distal region of the elongated structure. As the conducting members are insulated and extend from a proximal region to a distal region of the elongated structure, they include an elongated component of a conductive material, e.g., an electrically conductive material, which is surrounded on all sides, e.g., coated, with an insulating material. In some instances the elongated conductors include a pattern of insulation openings among the insulated conducting members at one or both of the proximal and distal regions, or even along intermediate regions along the length of the elongated conductor. By "pattern of insulation openings" is meant a collection of areas or windows (i.e., voids) among the insulation of the conductive members in the region of interest, e.g., proximal or distal region.

In certain embodiments, the elongated intravascular device for which the smart torquer is configured to manipulate is a device that includes an elongated conductor conductively, e.g., electrically, connecting, any two components, such as a proximal end connector and a distal end effector. Proximal end connectors may vary widely and are configured to serve as a connection between the elongated conductor (and effector coupled to the distal end thereof) and a contact of the smart torquer, e.g., as described below. In these embodiments, a variety of different effectors may be conductively coupled to the distal end of the elongated conductor. Effectors that may be coupled to the distal end of the elongated conductors may be sensors and/or actuators. Sensing effectors of interest, i.e., sensors, may be configured to sense a variety of different types of data, such as but not limited to: electrical conductivity data, electrical potential data, pressure data, volume data, dimension data, temperature data, oxygen or carbon dioxide concentration data, hematocrit data, pH data, chemical data, blood flow rate data, thermal conductivity data, optical property data, cross-sectional area data, change in structure data, viscosity data, radiation data, monitoring an actuation process, magnetic field indicators, and the like. Alternatively, the effectors may be configured for actuation or intervention, such as providing an electrical current or voltage, setting an electrical potential, providing a calibration signal, a test stimulation, a catheter tip localizing current, heating a substance or area, inducing a pressure change, releasing or capturing a material, emitting light, emitting sonic or ultrasound energy, emitting radiation, orienting a tip, pushing against a surface, opening/closing a fluid channel, releasing a coil, and/or the like.

In some instances, the effector is electrically coupled to the elongated conductor via circuitry element, such as an integrated circuit. When present, integrated circuits may include a number of distinct functional blocks, i.e., modules, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain embodiments of the present invention are distinct from hybrid integrated circuits, which are miniaturized electronic circuits constructed of individual semiconductor devices, as well as passive components, bonded to a substrate or circuit board, such as may be supported on an interposer, an intermediate printed circuit board, an HDI flexible circuit, etc.

The support with which the circuit is associated, e.g., by being present on surface of the support or integrated, at least partially, inside of the support, may be any convenient support, and may be rigid or flexible as desired. Where the support is intraluminal sized, its dimensions are such that it can be positioned inside of a physiological lumen, e.g., inside of a vessel, such as a cardiac vessel, e.g., a vein or artery. In certain embodiments, the intraluminal sized integrated circuits have a size (e.g., in terms of surface area of largest surface) of between about 0.05 mm$^2$ and about 10 mm$^2$, such as between about 0.5 mm$^2$ and about 8 mm$^2$, and including about 1.5 mm$^2$. The supports of the integrated circuits can have a variety of different shapes, such as square, rectangle, oval, and hexagon, irregular, etc.

Elongated intravascular devices having an elongated conductor with a connector at the proximal end and an effector at the distal end are further described in U.S. patent application Ser. No. 15/159,615 filed May 19, 2016 and U.S. Provisional Application Ser. No. 62/169,347 filed on Jun. 1, 2015; the disclosures of which are herein incorporated by reference.

Elongated intravascular devices that may be manipulated with smart torquers of the invention include, but are not limited to: intraluminal medical devices, i.e., medical devices configured to be introduced into a lumen of a subject to sense and/or modulate various physiological parameters, where examples of such devices include, but are not limited to catheter based devices, guidewire based devices, indwelling blood interfacing devices, pacing leads, surgical drains, interstitially placed cannulas, etc. An example of such a device is an interventional tool (e.g., a microsurgical tool) configured for monitoring electrophysiological activity within the vicinity of a lumen, the microsurgical tool including a one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962 published as WO2014160832 and titled "Neurological Traffic And Receptor Evaluation And Modification: Systems And Methods", the disclosure of which is herein incorporated by reference. Other such devices in which the elongated conductors find use include, but are not limited to: those devices described in: PCT application serial no. PCT/US2013/023157 published as WO 2013/112844 and titled "Controlled Sympathectomy and Micro-Ablation Systems and Methods"; PCT application serial no. PCT/US2013/042847 published as WO 2013/181137 and titled "Endoscopic Sympathectomy Systems and Methods"; PCT application serial no. PCT/US2013/045605 published as WO 2013/188640 and titled "Devices, Systems, And Methods for Diagnosis and Treatment of Overactive Bladder"; PCT application serial no. PCT/US2013/067726 published as WO 2014/070999 and titled: "Systems, Methods, And Devices For Monitoring And Treatment Of Tissues Within And/Or Through A Lumen Wall"; and PCT application serial no. PCT/US2013/073844 published as WO/2014/089553 and titled: "Systems and Methods for Regulating Organ and/or Tumor Growth Rates, Function, and/or Development"; the disclosures of which applications are herein incorporated by reference.

FIG. 1 provides a schematic illustration of an elongated intravascular device having an effector made up of a plurality of microfingers at a distal end, e.g., as further described in the various applications incorporated by reference above. In FIG. 1, elongated intravascular device 100 is a smart guidewire that includes a distal end effector 110 and a proximal end connector 120 separated from each other by a bridge 130 that houses a plurality of insulated electrically conducting wires. Effector 110 includes a plurality of microfingers that are configured to interact with the nerves in the vicinity of the lumen walls near a treatment/diagnostic site. Generally the plurality of microfingers may include a plurality of sensory elements that perform these interactions. Each of the microfingers is electrically coupled to a "core" circuitry element 116 via leads 114. Core 116 is configured to boost and/or digitize the signals captured from the microfingers and is also electrically coupled to the bridge 130, so as to interact with the outside world. Bridge 130 makes up the body of the smart guidewire and provides both mechanical and electrical interaction between the core 116 and the outside world. The bridge 130 has a connector 120 at the proximal end, is designed with mechanical properties to suit the application needs, and includes a plurality of wire elements to establish communication—power delivery between the core and an outside device. Connector 120 includes 4 distinct contacts 122a to 122d, e.g., in the form of ring electrodes, for operably contacting the contacts of a smart torquer, e.g., as described in greater detail below.

As summarized above, aspects of smart torquers of the invention include an engager for releasably engaging an elongated intravascular device; a communications module; a contact associated with the engager and configured to communicatively contact an elongated intravascular device engaged by the engager with the communications module; and a manipulator configured to allow a user to torque an elongated intravascular device engaged by the engager. Each of these components is now described further in greater detail.

The engager of the smart torquer is configured to releasably engage an elongated intravascular device, e.g., as described above. As such, the engager is configured to reversibly stably associate with a region or domain of an elongated intravascular device, such as the proximal end of an elongated intravascular device. The engager may include any of a variety of different types of reversibly stable association component(s), where such components may vary. Such components may include, but are not limited to: constrictors, retractable/deployable protrusions, retractable barbs, etc. In some embodiments, the reversibly stable association component is a constrictor, e.g., a rotatably actuatable constrictor having a diameter that restricts and widens in response to a rotatable actuator, e.g., a dial.

In addition to the reversible stable association component(s), the engager also includes a space for receiving a region or domain, e.g., distal end, of the elongated intravascular device. While the dimensions of this elongated intravascular device receiving space may vary, in some instances this space has a length ranging from 1 to 100 mm, such as 1 to 35 mm and a longest cross-sectional diameter ranging from 0.075 to 20 mm, such as 0.075 to 2 mm.

In some instances, at least a portion of the engager is configured to provide for electrical magnetic interference shielding. For example, the distal most portion of the receiving space and optionally the proximal most part, such that only a portion or all of the engager, may be configured to establish a closed shield around electrically conducting components, e.g., wires, of an elongated intravascular device when the proximal end of the device is present in the receiving space. The smart torquer can therefore be configured to provide a degree of enhanced shielding from outside EMI so as to improve the SNR of the signals communicated from the device to the smart torquer.

The engager further includes an entry port for receiving the proximal end of an elongated intravascular device into the receiving space of the torquer. The entry port may have a variety of different configurations, e.g., a hole, slit, etc., where the dimensions of the entry port may vary, so long as it is configured to receive the proximal end of a desired elongated intravascular device. Where the entry port is a hole, the hole may, in some instances, have a longest diameter ranging from 0.02 to 10 mm, such as 0.02 to 2 mm. In some instances, the entry port may be configured as a funnel, where the diameter of the funnel decreases from the distal to proximal end of the port, e.g., so as to guide the proximal end of an elongated intravascular device into a seal element of the engager.

Where desired, the engager may include a seal, which may be configured to fluidically seal a proximal end of the elongated intravascular device inside of the torquer. The seal may be configured to provide for passage of the proximal end of the elongated intravascular device through the seal, where when the proximal end of the device passes through the seal, the seal serves to wipe or clean the proximal end of the device, e.g., so as to remove blood or other fluids from the proximal end as it is inserted into the engager. This configuration may be advantageous for minimizing fluid deposition between the connectors within the coupling, thus maintaining a more reliable connection there-between, etc. When present, any convenient seal may be employed in the engager. In some instances, the seal is a foam/gel film that gets punctured by the proximal end of the elongated intravascular device, thus forming a water-tight septum seal around the proximal end of the device to keep fluids out during use. Alternatively the seal may be established with a microseal, e.g., as described at the website produced by positioning "http://www." before "merlinic.com/products/merlin-microseal/how-the-merlin-microseal-works". Some examples of such microseals include, but are not limited to: those devices described in: U.S. Pat. Nos. 4,954,149 and 5,5031,810; the disclosures of which are herein incorporated by reference. Additional and alternative seal components that may be employed in a given seal configuration include, but are not limited to: wiper rib, o-ring(s), or spring based duckbill valve into the tip, etc.

Another component of smart torquers of the invention is a contact component associated with the engager. The contact component is configured to operably contact with a corresponding contact element in an elongated intravascular device engaged by the engager. When operatively contacted with a corresponding device contact(s), the contact component provides for communication between the engaged device and the communications module of the smart torquer, e.g., either directly or via a processing component. By communicatively contact is meant that the contact is configured to provide for data transfer establishment between a contact(s) of the elongated intravascular device and the communications module of the smart torquer, e.g., as described in greater detail below. The nature of the connector may vary, where examples of types of connectors include, but are not limited to: electrical connectors, optical connectors, etc. In some instances, the contact is configured to provide electrical communication between the elongated intravascular device and the communications module. The particular configuration of a given contact component may vary, where the contact component may provide for digital, some power, optionally some analog, some chip select, etc., as desired. While the nature of the contact may vary, in some instances the contact includes one or more electrodes, e.g., one or more ring electrodes, which one or more electrodes is configured to be joined in electrical communication with one or more contacts of the proximal end of the elongated intravascular device.

Smart torquers of the invention further include a communications module, which module is operably coupled to the contact component of the smart torquer and provides for transfer of data received from an engaged elongated intravascular device to another component, e.g., an external device, etc. The communications module may be configured to provide for the transfer of data in a wired or wireless mode, as desired. Communications modules of the smart torquers may be configured, e.g., via hardware and/or software implementation, to perform desired communications functions, e.g., to receive data from a contact, to transfer data, e.g., to a USB port for wired communications or a wireless transmitter for wireless communications, etc. Communications modules are made up of one or more functional blocks which act in concert to perform a particular function, which is the purpose of the module. A given communications module may be implemented as hardware, software or a combination thereof. In some instances, the communications module may include a circuitry element, such as an integrated circuit. When present, integrated circuits may include a number of distinct functional blocks, i.e., modules, where the functional blocks are all present in a single integrated circuit on an intraluminal-sized support. By single integrated circuit is meant a single circuit structure that includes all of the different functional blocks. As such, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material.

Smart torquers may include a variety of different types of power sources that provide operating power to the device in some manner. The nature of the power source may vary, and may or may not include power management circuitry. In some instances, the power source may include a battery. When present, the battery may be a onetime use battery or a rechargeable battery. For rechargeable batteries, the battery may be recharged using any convenient protocol. In some applications, the smart torquer may have a battery life ranging from 0.1 to 10 hrs, such as 1 to 5 hrs.

As summarized above, smart torquers of the invention may include a manipulator configured to allow a user to torque an elongated intravascular device engaged by the engager. Any convenient type of manipulator may be present, where the manipulator may be configured to be gripped in a palm of a human hand; configured to be manipulated by fingers of a human hand, etc. A given manipulator may include ridges or other surface features to provide for grip between an operator and the torquer.

Figure 2:
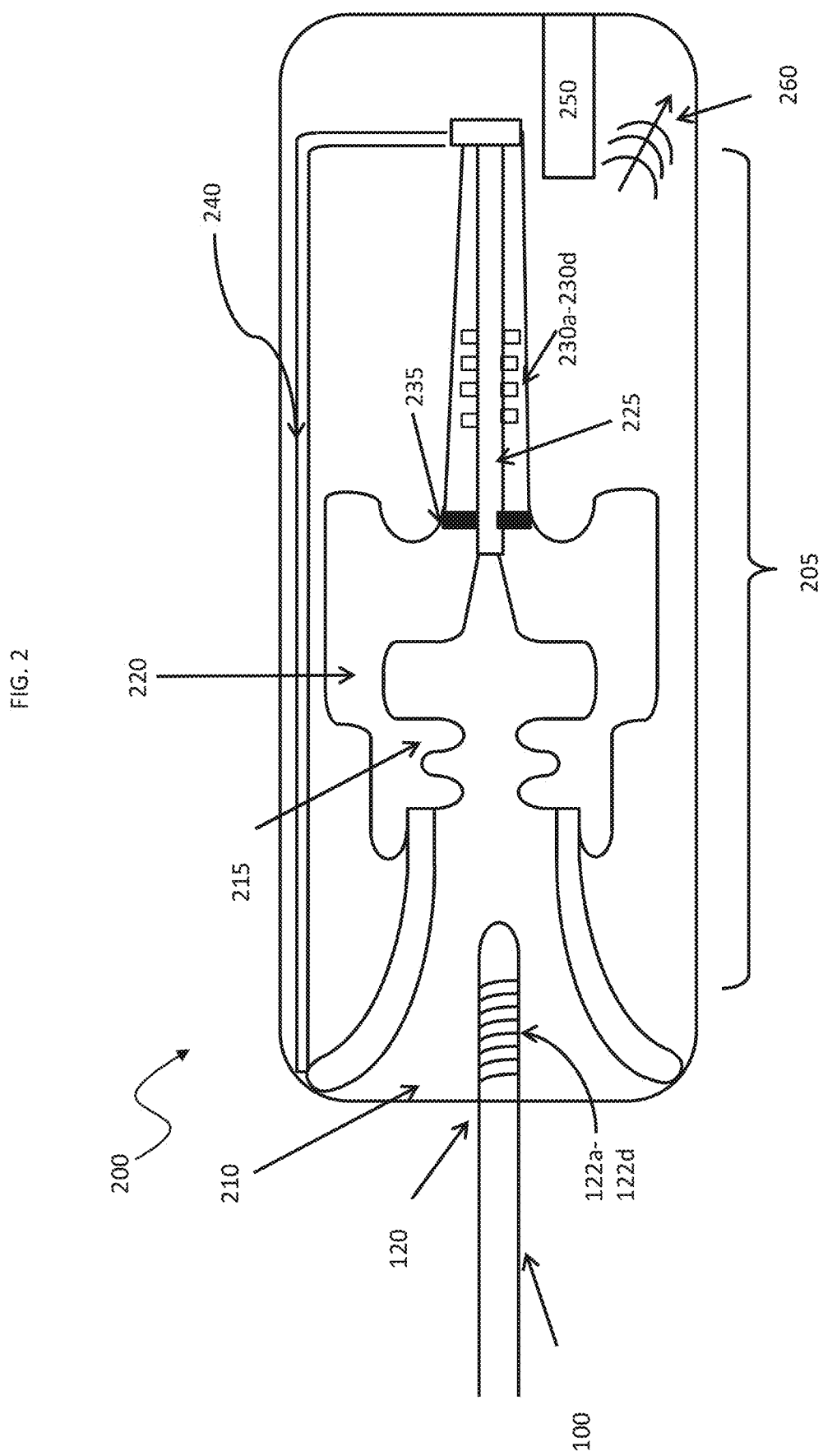
FIG. 2 provides a schematic illustration of a smart torquer according to an embodiment of the invention.

FIG. 2 provides a schematic illustration of a smart torquer 200 configured to operably engage an elongated intravascular device, such as the smart guidewire illustrated in FIG. 1. As shown in FIG. 2, smart torquer 200 includes an engager 205 having an entry port 210 which is configured to receive the proximal end 120 of the smart guidewire. As shown, entry port 210 is configured as a funnel. Engager 205 also includes an initial wiping component 215 which may be present and serve to remove excess fluid from the proximal end of the guidewire. Also shown is a rotatably actuatable constrictor 220 which may be tightened about the proximal end 120 of device 100 as desired in order to stably associate the device with the smart torquer. Engager 205 further includes receiving space 225 which includes four contact element configured to operably contact the contact elements 122a-122d of device 100. A seal 235 is present at the distal end of the receiving space 225. An RF shield 240 is provided about the distal end of the engager 205, e.g., to shield the conductors of the device 100 when engaged by the smart torquer. It is noted that, when present, the RF shield could also be integrated into the case body, but with a pass through for an externally positioned antenna, etc. Also shown is battery 250. Smart torquer 200 further includes a wireless communication module 260 which is operably connected to contacts 230a-230d of the smart torquer and is configured to provide for transfer of data received from an elongated intravascular device 100 to another component, e.g., an external device, etc.

The smart torquer may vary in overall dimensions, where in certain embodiments the smart torquer is configured to be hand-held. In such instances, the smart torquer may have a length ranging from 5 to 200 mm, such as 10 to 75. In a substantially cylindrical implementation, the smart torquer may have a longest diameter ranging from 2 to 60 mm, such as 10 to 25 mm. In the case of a substantially non-cylindrical implementation, the smart torquer may have a height ranging from 2 to 75 mm, such as 5 to 20 mm and a width ranging from 2 to 75 mm, such as 10 to 35 mm. The mass of the smart torquer may vary, ranging in some instances from 2 to 250 grams, such as 10 to 100 grams.

In some instances, the smart torquer may include one or more external connectors, so as to interconnect one or more body electrodes, with the communication module, to complete one or more circuits in the coupled catheter/guidewire, to provide a reference potential for the catheter/guidewire, to provide a body contact for the RF shield, or the like. In some instances, the smart torquer may include a current generator configured so as to communicate a current, an alternating current, a sinusoidal current (e.g., with frequency in the range of 10-600 kHz), to the one or more external connectors, the communication module and/or the guidewire/catheter configured so as to measure a return current, or local field potential associated with the generated current (i.e., so as to measure impedance between a sensing element on the catheter and the body electrodes, to detect leakage currents from the catheter or smart torquer to the body, etc.). Such sensing may be used to assess the quality of the EMI shield, to ensure contact or circuit integrity between the catheter, smart torquer and the body of the subject to which they are coupled, or the like. In some instances, the smart torquer may include circuitry configured to measure the impedance, field, or leakage current at the catheter tip, so as to localize the catheter tip within the body of the subject to which it is attached, to determine the location of the catheter tip between the placed electrodes, etc. In some instances, the smart torquer may include biosignal conditioning circuitry, coupled with the external contacts, configured so as to measure a biosignal from the external contacts (e.g. an EKG, EMG, pulse, local pulse, etc.). Such as signal may be conditioned and compared with signals conveyed from the associated catheter so as to provide a timing signal (e.g. so as to establish a heart rhythm and/or breathing rhythm time stamp against which to compare recorded neural traffic, and/or related sensory information collected by the catheter/guidewire). In some instances, such external signal collection may be conditioned and incorporated into the streamed signals from the associated catheter/guidewire so as to remove/analyze a movement component, or the like. Such a configuration may be advantageous to collect such additional biologic information and/or physiologically referenced time-stamps without the need for hardwiring of the smart torquer to an external device or having to establish a timing correlation between separate sensing systems. Such lack of physical connection may be advantageous to reduce EMI, reduce the chance of forming current loops, introduction of spurious signals, etc. into the signals conveyed by the catheter/guidewire.

Figure 3:
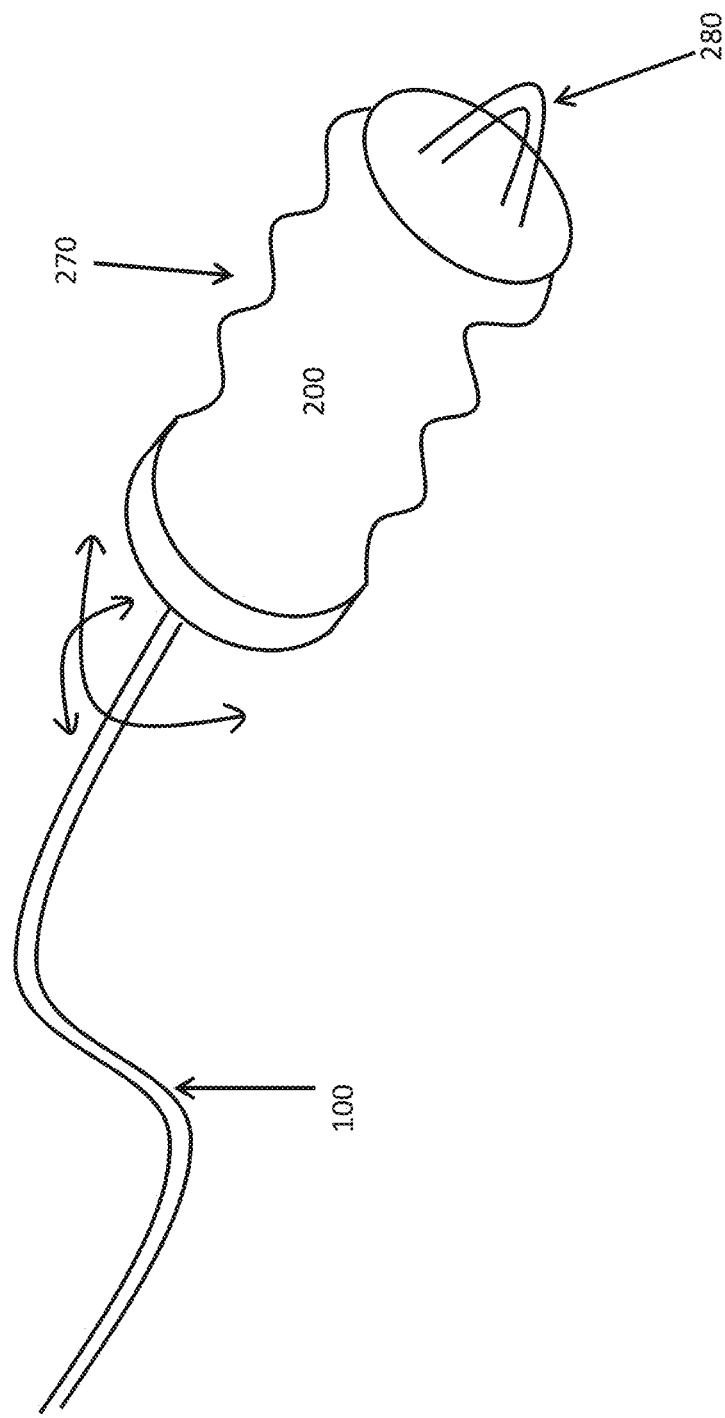
FIG. 3 provides a three-dimensional view of a smart torquer operably engaging a smart guidewire according to an embodiment of the invention.

FIG. 3 provides a view of a smart torquer 200 operably enaging a smart guidewire 100. Crossed arrows indicate the types of movement that smart torquer 200 is capably of imparting to the engaged smart guidewire 100. As shown, smart torquer includes handgrip 270, which is configured to be gripped by a human hand. Also shown is attachment element 280 which serves to attach the smart torquer to a bed rail during use. As such, in some instances, a smart torquer may include an attachment component, e.g., for attaching to a sheet, to a bed (e.g., a hospital bed), etc. The attachment component, when present, may vary, and in some instances may be a clip, snap, hook and loop attachment component, etc. In some instances, the smart torquer may include one or more indicators, including but not limited to an LED, a speaker, a buzzer, an alarm, etc. so as to indicate a state of operation, a battery life, a current leaking indicator, an interconnect quality with an associated catheter, etc. to an operator.

In some instances, the grip may be electrically insulated from the remainder of the torquer with sufficiently low capacitive coupling to an engaged by hand, such that minimal EMI may be transferred from an operator to the sensing hardware during use.

In some instances, the smart torquer may include an antenna arranged to an end of the torquer so as to facilitate wireless communication of data between the torquer and an external device, even when the torquer grip is engaged by the hand/fingers of an operator. In some instances, the smart torquer may include a capacitive sensor for detecting when an operator has engaged with the torquer.

In some instances, the smart torquer may be substantially flat, or gull-winged in shape. Such a shape may be advantageous for an operator to manipulate an associated guidewire with few fingers, to achieve a strong torque from a small device, etc. In some instances, the smart torquer may include a circuit board, the circuit board fashioned with an integrated connector, the outer regions of the circuit board extending into the gull-wings of the body of the torquer. Such a configuration may be advantageous for minimizing the complexity of the smart torquer hardware while providing a strong grip interface for an operator. Such a configuration may be advantageous for use as a cost effective, disposable smart torquer.

In those configurations where the elongated intravascular device is an elongated conductor, e.g., one that includes a distal end effector and a proximal end connector, such as described above and illustrated in FIG. 1, the smart torquer may be configured to provide for universal coupling to any of a variety of different types of such devices having a variety of different types of proximal end connectors. For example, the connector component of the smart torquer may be configured to be operably with elongated intravascular devices that include varying numbers of proximal end contacts, e.g., where the number of contacts may be 2 or more, such as 4 or more, 6 or more, 8 or more, 12 or more, 20 or more, 32 or more, etc. As such, a contact component of a given torquer of the device may include varying numbers of individual contact elements, where in some instances the number of individual contact elements of the device is 2 or more, such as 4 or more, 6 or more, 8 or more, 12 or more, 20 or more, 32 or more, etc. Between a given pairing of a smart torquer and a device, the number of contact elements in each may be the same or different, e.g., where the smart torquer may have more or less contacts than the corresponding elongated intravascular device.

A smart torquer may be configured to identify one or more properties of a given elongated intravascular device and, in response to the identified properties of the device, tailor its interface with the device and/or its operation, so as to optimally operate with the elongated intravascular device. For example, in some instances where there are more contacts on the smart torquer than on the elongated intravascular device, the smart torquer (and specifically a suitable module thereof, which may be implemented in any convenient way, such as described above) may be configured so as to interface with the contacts of the elongated intravascular device dependent on the number of contacts present in the device. For example, the smart torquer may include circuitry configured to determine the number of contacts and mating contact range on the elongated intravascular device, e.g., via an impedance based approach. For example, impedance between the distal most and proximal most contacts on the intravascular elongated device may be controlled such that a circuit closure can be monitored to ensure proper interconnection between the torquer and elongated intravascular device. In some instances, the controlled impedance may have a random component to it that may be used as a unique ID without having to allocate additional register space on a chip.

The elongated intravascular device may include an additional component connected between the distal most and proximal most contacts, the additional component may vary, wherein examples of such components include but are not limited to: a single blow fuse, a transponder, a one-time writeable transponder, etc. Such a configuration could be used for device identification, determining device reuse, etc., without actively affecting the device performance (the decision to continue to communicate with the device or not, can be made external to the device, the device itself only holds the needed information). In some instances, the smart torquer includes a circuit for communicating with an embedded microcircuit on an elongated intravascular device. Such a circuit may be configured to perform a number of different tasks, e.g., identify a given elongated intravascular device, identify the configuration of a given elongated intravascular device, determine whether a given elongated intravascular device has been used or not, etc. In aspects, the embedded microelectronics of a given elongated intravascular device may include one or more "usage" fuses, a series of single use fuses that are blown sequentially during power up/down, at timed events during a procedure, at procedure completion, or the like and can be read externally by a smarter torquer to determine if the device has already been used or not. The decision to deny use or report misuse, etc. may be made at the second device level, in a cloud server, etc.

The smart torquer may be configured to ensure suitable interconnection is made between the torquer contact(s) and the elongated intravascular device in a number of different ways. When mating an elongated intravascular device with a smart torquer, it is desirable to have the contacts properly aligned such that the corresponding device and torquer contacts are properly mated. Where desired, a feedback signal relating to the alignment can be made using any convenient configuration. For example, the following configuration may be included in the elongated intravascular device proximal connector. The distal most contact on the proximal connector of the device may be electrically coupled, within the body of the device, to the most proximal contact on the proximal connector. Thus, a reliable interconnection and localization of contacts may be established in the torquer by measuring when the impedance between two contacts is sufficiently low. This configuration allows for a consistent contact to be made between the torquer and the device, and allows for accommodation of an "initially" unknown number of contacts on the device. Such a configuration may also ensure that a Faraday cage is produced around the proximal end of the device (in such an example, the distal most contact of the proximal connector may be coupled to the body of the device so as to form a conductive shield around the inner wires). Furthermore, such a configuration may be useful in assessing the EMI and cage noise on the device during use. For example, the distal most connector may be coupled to the local reference, thus producing a shield around the wires in the device. At the same time, the distal field can be sensed with the most proximal connector wire (assuming the catheter body and wire are connected at the distal portion of the device), in order to assess the quality of the protection, but also to provide a distal field feedback signal if one is actively driving the reference for noise cancelation purposes.

Where desired, a smart torquer of the invention may include a switch network, which may be automatically configured to couple the right circuitry on the torquer with the corresponding contacts that are mated to the elongated intravascular device. The switch network may be configured based upon which contacts are registering as electrically connected in the contact array (i.e., the connected contacts on the device define the physical contact range on the device). For example, the connected contacts frame up the overall array of contact elements on the device, and the switch network may be configured between those contacts such that any digital communication lines, power lines, and/or analog signal lines are properly configured (i.e., as determined automatically in the case of a digital ID system (such as described below) or as determined by a user defined configuration (e.g., such as via a configuration process on the second device).

As mentioned above, smart torquers of the invention may be configured to be universal interfaces for smart elongated intravascular devices, e.g., as described above. In some embodiments, the smart torquer is configured to provide a fully digital interface with a known number or order of contacts for every elongated intravascular device. The contacts may include connections for power, and signal (digital signal, optionally with one or more chip select lines). The number and order of contacts on the elongated intravascular device may be fixed across all compatible devices, thus providing a universal interconnect, irrespective of the actual sensor configurations on the device.

The elongated intravascular device may include embedded microelectronics that act as the analog/digital front end for the sensing function(s). The device microelectronics may include a digital communication module for communicating exclusively in a digital format with the torquer. In this embodiment, the embedded microelectronics may include an identification register, and/or other unique distinguishing ID, such that when connected with the torquer, the device configuration information can be setup via the torquer (for example: a unique device ID may include information pertaining to the technical aspects of that family, e.g., how many sensors, sensor layout, sensor calibration parameters and zero settings, etc.). The torquer may then coordinate the front end data acquisition with the smart elongated intravascular device.

In yet other embodiments, the smart torquer may include circuitry to perform general signal handling operations, generate metrics from signals, etc., that can be configured after connection to an elongated intravascular device or after configuration information is provided on the second device (either via manual settings, or automatically, the torquer can adjust the signal handling of the incoming digital signals, so as to perform additional filtering, generate metrics, resample (e.g., decimate, compress, etc.), the signals, before communicating the results to the second device (e.g., a polygraph)). A given elongated intravascular device's embedded microelectronics may include configuration circuitry such that channel bandwidth, gain, offsets, linearity, channel selection, bias current settings, adjustable input configurations (single ended/differential inputs, etc.), sample clock adjustment, per channel oversampling, sample depth, low frequency noise/movement elimination circuits, that may be digitally configured before, or during use via communication with the torquer.

The smart torquer may also be configured to provide a digital interface with an elongated intravascular device having an initially unknown number of chip select lines. In such embodiments, the elongated intravascular device may include multiple individual chips (e.g., such as in high electrode count systems). In such systems the chips may be daisy chained and may be operated either with a half-duplex configuration (i.e., where an individual chip ID is called out before and after sending info), or a chip select is used to call out and collect data from each individual chip. In this case, the number of connected chips can be determined by the method above (i.e., to automatically determine the number of chip select lines at the time of connection, thus making it easier to operate on any device, irrespective of the number of sensors, embedded chips, etc.).

In some instances, the elongated intravascular device may include a series of digital and analog, or even all analog channels, each channel coming to a contact in the proximal connector. The method above can be used to determine how many are in a particular device, and the switch network in the torquer can be reconfigured on the fly to interface with the channels, irrespective of the actual configuration. The torquer can be configured to automatically configure itself to interface with the elongated intravascular device and reliably start collecting data.

Figure 4:
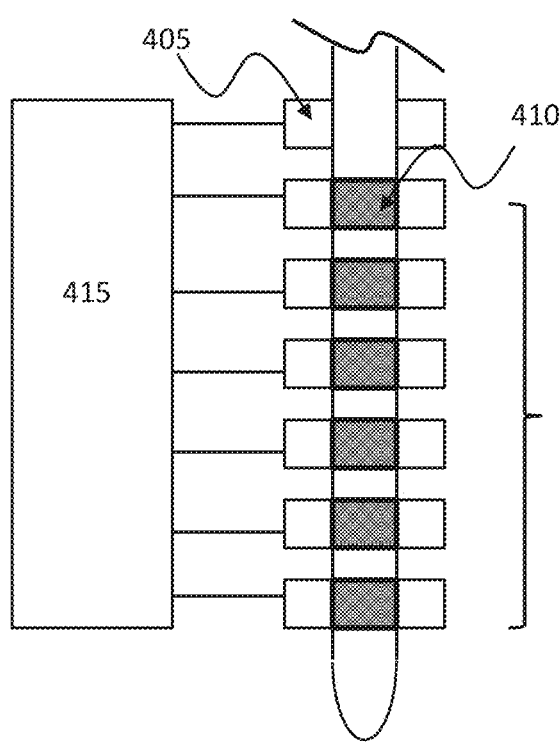
FIG. 4 illustrates an embodiment of a system of the invention in which the distal end of a smart guidewire includes fewer contacts than the contacts present in the smart torquer.

An example of a system where the distal end of a smart guidewire includes fewer contacts than the contacts present in the smart torquer is illustrated in FIG. 4. As shown in FIG. 4, the smart torquer includes 7 contacts 405 while the smart guidewire only includes 6 contacts 410. Each of the 7 smart torquer contacts 405 is coupled to a contact switch network 415. During engagement, the smart torquer checks impedance between contacts to identify which contacts are operably contacted to the device contacts, and thereby operate with the engaged device correctly.

Figure 5:
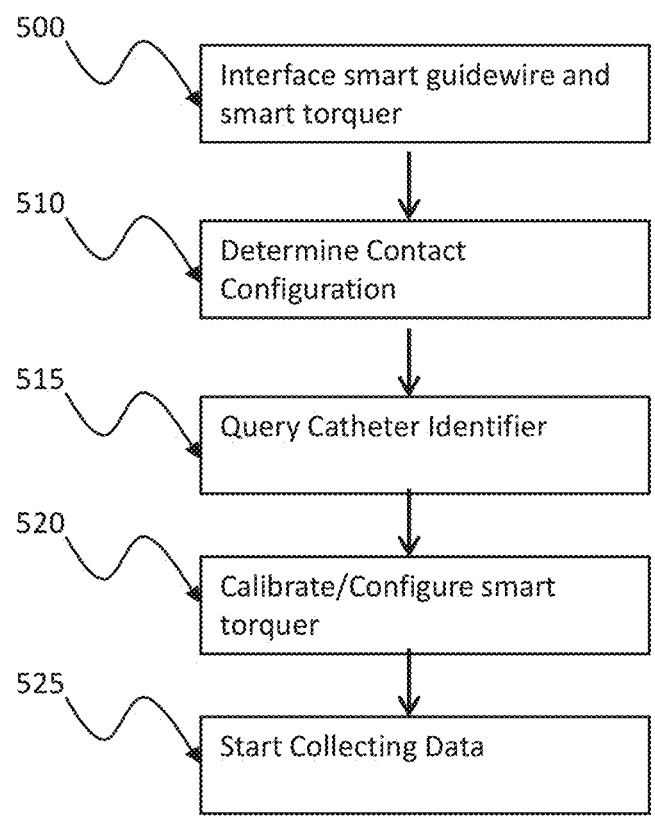
FIG. 5 provides a flow chart showing the steps that a smart torquer may take in establishing an operable engagement with a smart guidewire, in accordance with an embodiment of the invention.

FIG. 5 provides a flow chart showing the steps that a smart torquer may take in establishing an operable engagement with a smart guidewire. Initially at step 500 the proximal end of the smart guidewire is introduced into the engagement element of the smart torquer to interface the smart guidewire with the smart torquer. Next, at step 510, the contact configuration between the smart torquer and the smart guidewire is determined, e.g., by using the protocol described above in connection with FIG. 4. Step 515 is optional and may include querying the smart guidewire identifier with the smart torquer. Step 520 is also optional and may include calibrating/configuring the smart torquer for use with the specific smart guidewire, e.g., based on information obtained from querying the identifier. Finally, at step 525 the smart torquer can start receiving data from the smart guidewire.

In some instances, a smart torquer may be configured to selectively operate a portion of the effectors of an engaged elongated intravascular device that includes a plurality of effectors. For example, a given elongated intravascular device may have many individual sensors coupled to its distal end (e.g., 16 electrodes, 256 electrodes, etc.). During use, a viable and useful signal may be present on only a subset of the sensors (e.g., such as 2 sensors, 5 sensors, etc.), and/or a particular sensor may have an important, but very low amplitude signal on it (e.g., such as an approximately 10 μV extracellular action potential signal). To address such scenarios, the embedded microelectronics may include a variety of operating modes, such as a seek mode, a targeted mode, a quiet mode, and a movement compensation mode, of operation. In a seek mode, signal from all electrodes (each electrode representing a channel) is routed to the smart torquer for analysis at a certain bit-depth per channel (e.g., 8 bit, 10 bit, 12 bit, 16 bit, etc.). Such a mode is ideal for finding sites near the electrodes with "hot" neural traffic. In a targeted mode, a number of channels are selected that are near "hot" neural traffic, the remaining channels are temporarily shut down, and the selected channels are oversampled, so as to increase the bit depth on the selected channels. Such oversampling may be 4×, 16×, 128×, 256×, per channel, and the effective bit depth may be the original bit depth plus 1 bit, 2 bits, 3 bits, 4 bits, etc. (dependent on the degree of oversampling and the reconstruction algorithm employed in each specific case). Such a configuration may be advantageous to obtain additional bit depth out of a few important channels during an application. In a quiet mode, the bias, chopping frequencies, etc. are altered (generally but not always, bias currents are increased, chopping frequencies increased, chopping timing staggered, etc.), which can consume considerably more current, but which will drop the inherent noise floor for each channel, which can be used to increase the signal fidelity on each channel. Such an approach may be coupled with the targeted mode, such that only a few channels are powered on and analyzed during the quiet mode operation. In a movement compensation mode, a low frequency movement signal is captured on one or more of the channels (such as via a pressure sensor reading, from an electrode in the blood flow, from an electrode against a wall, etc.), and routed internally to the embedded microelectronics as a local reference for one or more of the other channels, thus allowing for elimination of the "movement" or other low frequency signal seen on the selected channel. The effect may also be performed digitally on the chip or on the torquer, but an analog implementation allows one to dramatically boost the channel gains on the remaining channels prior to digitization, and obtain higher fidelity signals off from of those channels during use. Such an approach may be advantageous for increasing signal fidelity of neural traffic recordings by removing movement related artifacts from signals directly at the source prior to quantization of the signals.

In those configurations where the elongated intravascular device is an elongated conductor, e.g., one that includes a distal end effector and a proximal end connector, such as described above, the smart torquer may be configured to provide for electrostatic discharge (ESD) protection. In such instances, the smart torquer may include ESD protection on each channel that is present in the configuration, such that, once connected, the elongated intravascular device and the torquer are protected against a high field ESD discharge (i.e., such that the combined system exceeds IEC 61000-4-2 requirements for use in a dry environment). Where desired, the smart torquer may be configured to monitor incoming and outgoing current into/out of the elongated intravascular device, e.g., for leakage detection, EMI protection, etc. An indicator, e.g., for alerting a user to the state of the contact between the torquer and the elongated intravascular device may be provided. The indicator may be an audible and/or optical indicator, i.e., an indicator that provides for a sound and/or light signal, respectively. The indicator may be configured to alert a user to a situation where the elongated intravascular device is and/or is not correctly coupled, i.e., operatively coupled, to the smart torquer.

Smart torquers of the invention may be disposable or reusable. As such, smart torquers of the invention may be entirely reusable (e.g., be multi-use devices) or be entirely disposable (e.g., where all components of the device are single-use). In some instances, the device can be entirely reposable (e.g., where all components can be reused a limited number of times). Each of the components of the device may individually be single-use, of limited reusability, or indefinitely reusable, resulting in an overall device or system comprised of components having differing usability parameters.

Figure 6:
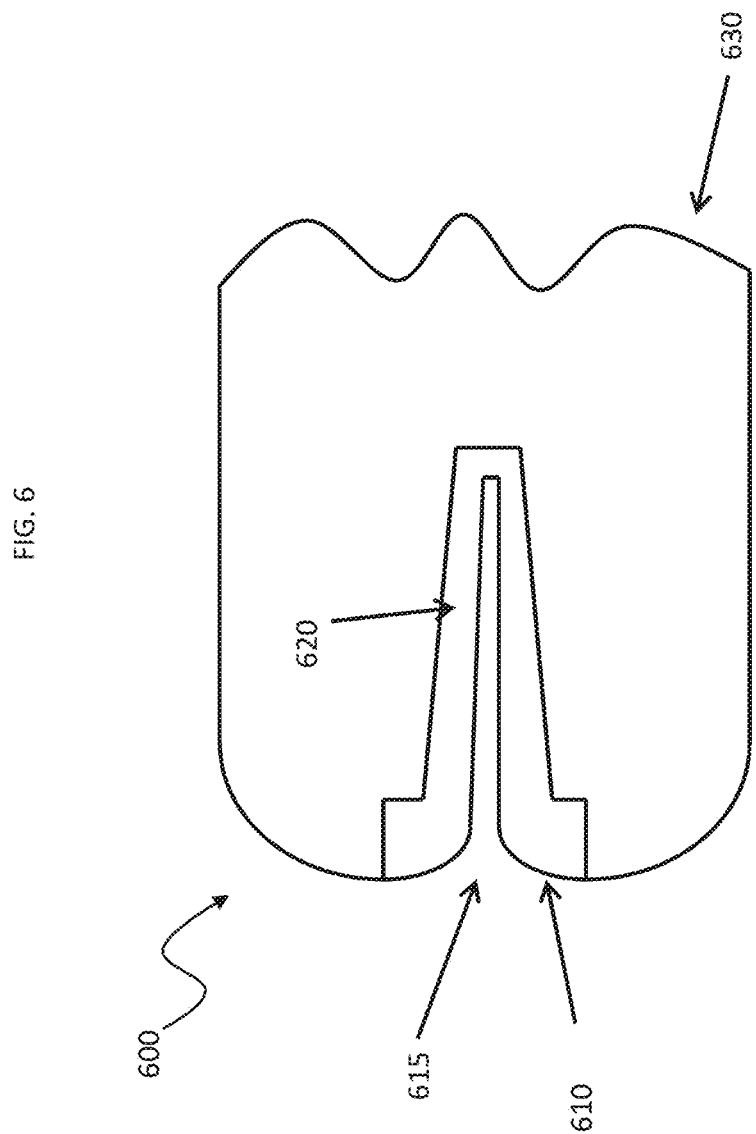
FIG. 6 provides an illustration of a one-time use portion of a smart torquer, in accordance with an embodiment of the invention.

In some instances, at least a portion of the device is configured for one-time use and at least a portion of the device is reusable. For example, a smart torquer may include a one-time use portion made up of the engager having a receiving chamber and a contact subcomponent (e.g., a microconnector). Where desired, the one-time use portion may further include a sterile casing, e.g., a bag, etc., which is configured to be positioned over a re-usable part of the smart torquer during use. An example of such a one-time use portion is illustrated in FIG. 6. As shown in FIG. 6, one-time use portion 600 includes an engager component 610 having an entry port 615 and a proximal end receiving portion 620, wherein the proximal end receiving portion 620 includes one or more microconnectors, not shown. Also shown in FIG. 6 is sterile bag component 630 which is configured to be placed over a re-usable portion of the smart torquer, e.g., as shown in FIG. 7 below.

In such instances, the reusable portion may include a contact subcomponent (e.g., macroconnectors) and the communications module. The contact subcomponents of the one-time use and reusable portions may be configured to interact with each other when assembled to provide for a complete contact. In some instances, the reusable portion may further include a power source. As such, in some instances the disposable portion may include the seal, a microconnector, and a grip actuator, with a sterile bag. The reusable portion may include an accompanying macroconnector, microcircuitry for communication, signal conditioning, memory, signal analysis, power management, and/or wireless communication to a nearby piece of equipment. The reusable portion could be coupled into the microconnector via the macroconnector and then sealed within the bag without having to compromise sterility of the overall setup. The bag may include a snap through connector to couple with the reusable portion, so that the snap through connector creates one or more contact points that could be attached to the bedding, anchored to a fabric site, etc. around the patient during the procedure.

Figure 7:
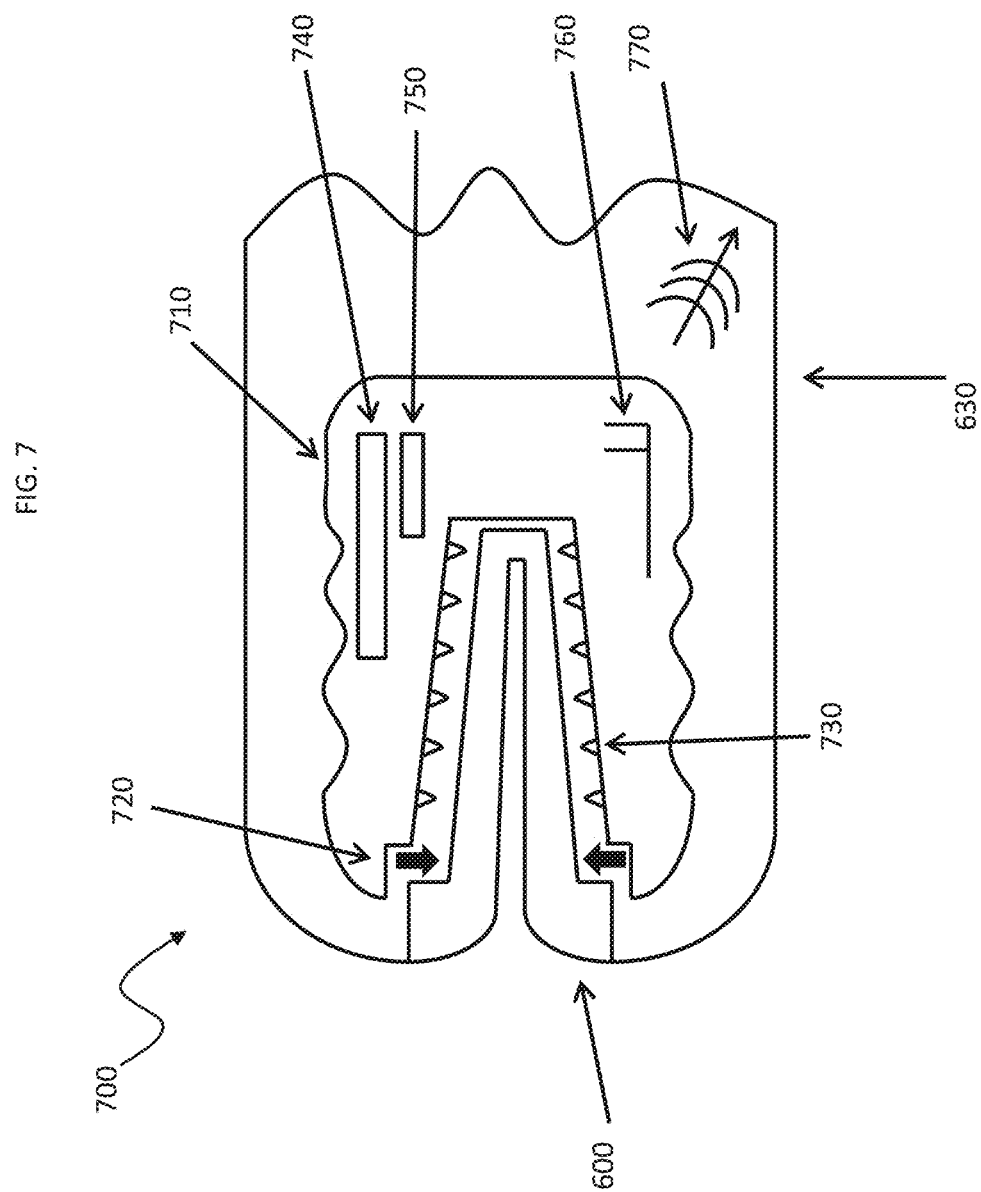
FIG. 7 provides a view of a smart torquer that includes one-time use portion operably configured with a re-usable portion, according to an embodiment of the invention.

An example of such a smart torquer is shown in FIG. 7. In FIG. 7, smart torquer 700 includes one-time use (i.e., disposable) portion 600 (as illustrated in FIG. 6) operably configured with a re-usable portion 710. Reusable portion 710 includes a constrictor 720 to reversibly stably associate the proximal end of a smart guidewire into the receiving portion of the device. Also shown are macroconnectors 730 for establishing electrical connection with the microconnectors of the disposable portion. Re-usable portion 710 further includes battery 740, circuitry component 750, RF antenna 760 and wireless communications module 770. As illustrated in FIG. 7, sterile bag component 630 of the disposable component 600 fits over and envelopes the re-usable portion.

Smart torquers of the invention may include a connector for coupling a body reference electrode to the smart torquer. Any convenient body reference lead connector may be present in the device. In some instances, the body reference coupling may be integrated such that it can rotate freely from the body of the smart torquer, so that the user can orient the smart torquer freely without the body reference lead getting tangled up in the assembly during use. The connector may be configured to operably connect to any convenient body reference electrode. For example, the body reference electrode may include a gel electrode and lead for attachment to the body of a subject, the gel electrode coupled (optionally via a circuit) to one or more of the contacts of the smart torquer, e.g., so as to establish a strong external reference on the patient for noise cancelation. Where desired, the torquer may include a slip ring contact to interface with the gel electrode lead, so as to maintain contact even during several rotations during use (to prevent tangling of that lead). An example of such a smart torquer and system including the same is illustrated in FIG. 8. As shown in FIG. 8, smart torquer 800 is operably engaged to a smart guidewire 810 which is inserted into the vasculature of patient 820. While the embodiment shown in FIG. 8 illustrates a femoral access of the guidewire, radial access may also be employed as desired. The smart torquer 800 includes a clip 830 for attached to a bed rail. Also shown is reference electrode 840 which connected to the smart torquer by a reference lead, e.g., as described above. Smart torquer 800 is in wireless communication with a display 860.

In some embodiments, the torquer may include a second engager configured so as to slidingly detach from the torquer and be slidingly positionable along the elongated intravascular device, and reversibly attached thereto, with a gripping member for a user to manipulate the second engager so as to provide a second contact point along the length of the elongated intravascular device for applying torque to the device. Such a configuration may be advantageous when a considerably long section of the device is positioned outside the body, and torque application nearer to the introducer is desired.

Smart torquers as described here may include one or more lumens or passageways, e.g., that are configured to align with one or more lumens or passageways of an elongated device, e.g., to provide for introduction of fluids into the elongated device, to provide for passage of tools to the distal end of the elongated device, etc.

Methods of Use

Smart torquers of the invention, e.g., as described above, find use in methods of operating elongated intravascular devices, e.g., smart catheters and guidewires, such as described above. In practicing methods of the invention, the proximal end of an elongated intravascular device is inserted through a port and into a receiving space of an engager of the smart torquer. Following insertion, the proximal end may be stably engaged in the engager, e.g., by actuating a stable engagement element, such as described above. Following stable engagement, establishment of contact between the device and the smart torquer may be confirmed as desired. In some instances, the engager is coupled to the intravascular device prior to removal of the intravascular device from any sterile packaging in which the device may be present. The elongated intravascular device may then be manipulated via the stably associated smart torquer, as desired.

One type of medical device with which smart torquers of the invention find use is intraluminal medical devices, i.e., medical devices configured to be introduced into a lumen of a subject to sense and/or modulate various physiological parameters, where examples of such devices include, but are not limited to catheter based devices, guidewire based devices, etc. An example of such a device is an interventional tool (e.g., a microsurgical tool) configured for monitoring electrophysiological activity within the vicinity of a lumen, the microsurgical tool including a one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962 published as WO2014160832 and titled "Neurological Traffic And Receptor Evaluation And Modification: Systems And Methods", the disclosure of which is herein incorporated by reference. Other such devices in which the elongated conductors find use include, but are not limited to: those devices described in: PCT application serial no. PCT/US2013/023157 published as WO 2013/112844 and titled "Controlled Sympathectomy and Micro-Ablation Systems and Methods"; PCT application serial no. PCT/US2013/042847 published as WO 2013/181137 and titled "Endoscopic Sympathectomy Systems and Methods"; PCT application serial no. PCT/US2013/045605 published as WO 2013/188640 and titled "Devices, Systems, And Methods for Diagnosis and Treatment of Overactive Bladder"; PCT application serial no. PCT/US2013/067726 published as WO 2014/070999 and titled: "Systems, Methods, And Devices For Monitoring And Treatment Of Tissues Within And/Or Through A Lumen Wall"; and PCT application serial no. PCT/US2013/073844 published as WO/2014/089553 and titled: "Systems and Methods for Regulating Organ and/or Tumor Growth Rates, Function, and/or Development"; the disclosures of which applications are herein incorporated by reference.

As disclosed in the above applications, use of such devices may include contacting the effector, e.g., sensor and/or actuator, of such a device to a tissue location of a living subject. Contact of the effector with tissue may be achieved via a variety of different protocols depending on the location of the target tissue, e.g., where the target tissue is internal, contact may be achieved via an intravascular approach. The devices may be employed with a variety of different types of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain embodiments, the subjects are humans. The methods may be diagnostic and/or therapeutic methods.

When a smart torquer is operably engaged to an elongated intravascular device, e.g., as described above, the resultant operable combination may be referred to a system. During use, a given system may include one or more additional components. For example, the system may further include a second device in communication with the communication module, where the communication may be wired or wireless, e.g., as described above. The second device may vary greatly, where the second may be configured to provide one or more functionalities, such as but not limited to, control of the elongated intravascular device, processing data obtained from the elongated intravascular device, displaying data obtained from the elongated intravascular device, e.g., in the form of a graphical user interface (GUI) or polygraph, etc. As such, a given second device of the system may include a controller for the elongated intravascular device, a data display, e.g., in the form of a monitor that provides a GUI or a polygraph output, etc. An example of a system of the invention is illustrated in FIG. 8, which is reviewed above.

Utility

Smart torquers of the invention, e.g., as described above, find use with a variety of different elongated intravascular devices, e.g., smart catheters and guidewires, and the like. One type of medical device with which smart torquers of the invention find use is intraluminal medical devices, i.e., medical devices configured to be introduced into a lumen of a subject to sense and/or modulate various physiological parameters, where examples of such devices include, but are not limited to catheter based devices, guidewire based devices, etc. An example of such a device is an interventional tool (e.g., a microsurgical tool) configured for monitoring electrophysiological activity within the vicinity of a lumen, the microsurgical tool including a one or more distinct sensing and/or actuating elements, e.g., in the form of microfingers, having a substantially elongate structure configured so as to bias a region thereof against a wall of the lumen upon deployment within the lumen, and a sensing tip electrically and mechanically coupled to the microfinger in the vicinity of the region, configured to interface with the wall of the lumen, the sensing tip configured to convey one or more electrophysiological signals associated with the activity. Such devices are further described in PCT application serial no. PCT/US2014/031962 published as WO2014160832 and titled "Neurological Traffic And Receptor Evaluation And Modification: Systems And Methods", the disclosure of which is herein incorporated by reference. Other such devices in which the elongated conductors find use include, but are not limited to: those devices described in: PCT application serial no. PCT/US2013/023157 published as WO 2013/112844 and titled "Controlled Sympathectomy and Micro-Ablation Systems and Methods"; PCT application serial no. PCT/US2013/042847 published as WO 2013/181137 and titled "Endoscopic Sympathectomy Systems and Methods"; PCT application serial no. PCT/US2013/045605 published as WO 2013/188640 and titled "Devices, Systems, And Methods for Diagnosis and Treatment of Overactive Bladder"; PCT application serial no. PCT/US2013/067726 published as WO 2014/070999 and titled: "Systems, Methods, And Devices For Monitoring And Treatment Of Tissues Within And/Or Through A Lumen Wall"; and PCT application serial no. PCT/US2013/073844 published as WO/2014/089553 and titled: "Systems and Methods for Regulating Organ and/or Tumor Growth Rates, Function, and/or Development"; the disclosures of which applications are herein incorporated by reference.

Another type of device with which smart torquers of the invention may be employed is a solid-state pressure measurement device. Such devices may be configured as guidewires and catheters, and utilize distal solid-state pressure transducers to obtain a body pressure measurement of interest, such as blood pressure (or other fluid pressure) measurements. In some instances these devices include piezoresistive sensors that operate in conjunction with a Wheatstone bridge circuit (e.g., a half-bridge configuration). For use with such devices, a smart torquer may therefore house the necessary electronics and other equipment to allow a solid-state pressure transducer located on an interventional device (such as at the distal tip) to function. For example, a smart torquer may house the necessary electronics for supplying a proper excitation voltage ("bridge input;" e.g., such as 2-10 VDC for medical transducers) to a Wheatstone bridge circuit. In such instances, a smart torquer may house an electrical completion network for the Wheatstone bridge circuit (e.g., the remaining two resistors of a half-bridge circuit and the bridge output connections). In such instances, a smart torquer may house appropriate electrical contacts/connections for conductors passing from a distal end of the device through the device shaft to the smart torquer, allowing for electrical signals to pass between the sensor and smart torquer circuitry. A smart torquer in such instances may contain all other necessary electronics for wireless use of such interventional pressure-sensing devices, such as an A/D converter, microcontroller, wireless communications module, power source, etc. Examples of solid state pressure measurement devices that may be configured to be employed with smart torquers of the invention include, but are not limited to: the PressureWire Aeris Wireless FFR pressure sensing device (St. Jude Medical); the PrimeWire Prestige and Verrata pressure sensing devices (Volcano); Mikro-Tip catheter pressure sensing devices (Millar), etc.

Another type of device with which smart torquers of the invention may be employed is an optical pressure measurement device. Such devices may be configured as guidewires and catheters, and utilize optical pressure sensors, such as a Fabry-Perot chip sensor, to obtain a body pressure measurement of interest, such as blood pressure (or other fluid pressure) measurements. Such sensors include optical and electro-optical systems and components, such a light source, photodetector, optical waveguides, etc., to perform pressure measurement. For use with such elongated devices, smart torquers of the invention may house necessary electronic, electro-optical, and optical elements to allow an optical pressure sensor located on an interventional device to operate while maintaining wireless functionality. In such instances, smart torquers may contain an embedded light source, such as a light-emitting diode (LED), laser diode, superluminescent diode (SLD), white light source, and the like, which produces the light waves that are carried to the optical sensor. Smart torquers may also include a photodetector, such as a photodiode, etc., which is configured to receive light waves returning from the optical pressure sensor and to transduce light energy into corresponding electrical signals. In such instances, the smart torquer may house optical wave guides, such as optical fibers, that align and splice (i.e., interface or couple) with optical fibers contained in the interventional device when the smart torquer is connected to the interventional device, such that the optical fibers are in communication, allowing light to pass between the smart torquer and interventional device through the optical fibers. Where desired, the smart torquer may contain specific assemblies for mechanically splicing two optical fibers together when the smart torquer and interventional device are joined, such that the fibers are properly aligned and interfaced, allowing light to pass from one to another. Examples of such assemblies are alignment sleeves, capillary tubes, fiber optic ferrules, fiber optic connectors, etc. These assemblies can be configured to allow for non-permanent interfacing of optical fibers such that the smart torquer can be both connected to and disconnected from the interventional device. In such instances, smart torquer may contain optical components for properly coupling/focusing light from the light source into an optical fiber (input coupling) and from an optical fiber to a photodetector (output coupling). Examples of such components include collimators, lens systems, etc. As desired, smart torquers may contain all other necessary electronics for wireless use of such optical pressure-sensing devices, such as an A/D converter, microcontroller, wireless communications module, power source, etc. Alternatively or in addition, smart torquers may include the hardware needed to drive the optical components, and the optical components may be integrated into a mating catheter/guidewire. Examples of optical pressure measurement devices that may be configured to be employed with smart torquers of the invention include, but are not limited to: the OptoWire One pressure sensor (Opsens Medical), the RXi Rapid Exchange FFR System pressure sensor (Navuus MicroCatheter—ACIST Medical Systems), etc.

Smart torquers of the invention also find use with elongated devices that include lumens and ports, such as catheters that contain one or more hollow lumens passing through the device, such as from a proximal port to the distal tip. Such lumens may serve a variety of purposes. For example, hollow lumens may allow for fluid removal from a patient, delivery of a fluid/drug/contrast agent into a patient, inflation of a distal balloon, passage of a catheter through the vasculature over an indwelling guidewire (i.e., a guidewire lumen), etc. In such instances, a smart torquer may contain one or more hollow lumens that align and interface/join with a corresponding lumen or lumens contained in the interventional device when the smart torquer is connected to the interventional device, such that the lumens are in communication. A smart torquer lumen interfaced/joined with an interventional device lumen effectively forms one continuous lumen extending throughout, allowing the lumen to be used for its purpose while leaving the smart torquer connected to the interventional device. In such instances, the smart torquer may have a lumen that interfaces/joins with the lumen of an interventional device at one end while extending to the exterior of the smart torquer housing at the other end. At this point of the exterior housing, there may be a port connected in communication with the lumen for injection and/or removal of fluid. For example, the port may be a Luer lock port so that a syringe may be connected to the port and used for fluid delivery and/or removal. Thus, an operator may connect a syringe or similar device to the smart torquer port, and fluid may then be delivered from the smart torquer to the distal end of the interventional device and into a patient via the continuous lumen. Likewise, fluid may be withdrawn from the patient, passing from the distal end of the interventional device back to the smart torquer port via the continuous lumen. Therefore, an operator may perform fluid delivery and/or removal with the interventional device while the smart torquer remains connected to the interventional device, using the smart torquer as the access point. The smart torquer may have a lumen that interfaces/joins with the lumen of an interventional device at one end while extending to the exterior of the smart torquer housing at the other end. The continuous lumen may be then used as a guidewire lumen. For example, the smart torquer may be connected to a catheter, such as an over-the-wire catheter, and the catheter may then be advanced over a guidewire into the vasculature of a patient, and the guidewire may pass through the smart torquer and out of a port on the smart torquer housing. Therefore, an operator may deliver an interventional device into a patient (e.g., into the vasculature) while the smart torquer remains connected to the interventional device. For use with lumen containing elongated devices, the smart torquer may have a single lumen that joins with a single interventional device lumen, or the smart torquer may contain multiple lumens for joining with multiple interventional device lumens. A smart torquer lumen may be joined with an interventional device lumen using a variety of approaches. For example, the smart torquer lumen may have a segment that acts as a male end and slides into the interventional device lumen that acts as a female end (male-to-female connection). Another possibility is that smart torquer lumen and interventional device lumen may be joined end-to-end, which may involve a coupling component to align the lumens and hold them together. In any case, a mechanical seal and or seals may be employed. Also, in any case, lumen connections may be non-permanent such that the smart torquer can be both connected to and disconnected from the interventional device. A given smart torquer lumen may have multiple uses that correspond with the uses of the interventional device. For example, a lumen may enable withdrawal of a body fluid, for delivery of fluids/drugs/contrast agents, for inflation of a distal balloon, for passage over a guidewire, etc. Additionally, the lumen of the smart torquer, when connected to an interventional device, may allow for insertion of a second interventional device that performs a specific function, such an ablation catheter. For example, the smart torquer may be connected to an electrophysiology (EP) mapping catheter with a continuous lumen throughout, as previously described, and an ablation device may then be inserted through the lumen into the patient for simultaneous use of the interventional devices (e.g., mapping before, during, and after ablation), while maintaining use of the smart torquer for manual handling and wireless transmission of data.

In some instances, the lumen containing elongated device is a neurosensing guidewire, e.g., as described above. These neurosensing guidewires may contain a central lumen for drug delivery, contrast agent delivery, or other use. Smart torquers configures for use with such devices may contain a lumen that joins with the neurosensing guidewire lumen using the methods and design aspects described, forming one continuous lumen extending throughout and allowing the lumen to be used for its purpose while leaving the smart torquer connected to the neurosensing guidewire. An external port (e.g., a Luer lock port) on the smart torquer, positioned in communication with the lumen, may then be used as a point of injection for passing fluids through the neurosensing guidewire and into the patient. In some instances, the continuous lumen may allow for insertion of a second interventional device, such as an ablation device, while maintaining use of the smart torquer, as described previously.

Another type of device with which smart torquers of the invention may be employed is a fluid filled pressure measurement device. Such devices may be configured as guidewires and catheters, and commonly contain a hollow lumen extending throughout the length that can be filled with a fluid, such as saline. Pressure can then be transmitted from the distal end of the device (at the opening of the lumen) through the static fluid column (i.e., the fluid-filled lumen) to the proximal end of the device. The proximal end of the device may include a pressure transducer in communication with the fluid column to sense the transmitted pressure. Alternatively, the fluid column may continue from the proximal end of the device to an external pressure transducer (e.g., through a port/tubing connecting the proximal end of the device to the transducer). Smart torquers of the invention may be configured to house the necessary components for use with such devices, such as a hollow lumen, a flush port, a pressure transducer, and associated electronics, to enable fluid-filled pressure measurement when connected to an interventional device. In such instances, smart torquers may contain a hollow lumen that aligns and interfaces/joins with a corresponding lumen contained in the interventional device when the smart torquer is connected to the interventional device, such that the lumens are in communication. A smart torquer lumen interfaced/joined with an interventional device lumen effectively forms one continuous lumen extending throughout, e.g., for fluid-filled pressure measurement. At the exterior housing of the smart torquer, there may be a port connected in communication with the lumen for injection and/or removal of fluid. The port may be a Luer lock port so that a syringe may be connected to the port and used for fluid flushing. Thus, an operator may connect a syringe or similar device to the smart torquer port, and fluid may then be flushed through the continuous lumen from the smart torquer to the distal end of the interventional device, priming the continuous lumen with fluid to prepare the device for fluid-filled pressure measurement. Where desired, the smart torquer may house a pressure transducer positioned in physical communication with the static fluid column (i.e., the fluid-filled lumen), such that pressure transmitted from the distal end of the interventional device through the continuous fluid-filled lumen to the smart torquer located at the proximal end of the interventional device may be sensed by the transducer. While pressure transducers may vary, in some instances the pressure transducer is a solid-state pressure transducer, such as a piezoresistive sensor. Alternatively, the pressure transducer may be one of many other types of pressure sensors, such as an optical pressure sensor, e.g., as described above. Smart torquers configured for use with such devices may house the necessary electronics and components to enable the pressure transducer to function. For example, a smart torquer may contain excitation voltage circuitry, Wheatstone bridge circuitry, etc. for a piezoresistive sensor. A given tmart torquer may contain all other necessary electronics for wireless use of such fluid-filled pressure-sensing devices, such as an A/D converter, microcontroller, wireless communications module, power source, etc. Examples of fluid filled measurement devices that may be configured to be employed with smart torquers of the invention include, but are not limited to: Scimed Informer Wire pressure sensor (Scimed Inc.); Swan-Ganz Catheter pressure sensor (Edwards Lifesciences) etc.

Another type of device with which smart torquers of the invention may be employed is a thermodilution flow measurement device. Such devices may be configured as guidewires and catheters, and allow for a bolus of fluid to be delivered at a controlled volume and temperature into the blood stream, where such devices may include one or more temperature sensors, such as thermistors, that detect changes in temperature as blood is flowing. Smart torquers for use with such devices may include the necessary components to enable blood flow rate measurement via to thermodilution method. These components may include the necessary electronics to allow temperature sensors (e.g., thermistors) to function in addition to a hollow lumen and injection port. In such instances, smart torquers may contain a hollow lumen that aligns and interfaces/joins with a corresponding lumen contained in the interventional device when the smart torquer is connected to the interventional device, such that the lumens are in communication, e.g., as described above. In these embodiments, the purpose of the lumen is for injection of a bolus of fluid for blood flow measurement via thermodilution. At the exterior housing of the smart torquer there may be a port connected in communication with the lumen for injection of fluid, as described above. Thus, an operator may connect a syringe or similar device to the tmart torquer port, and a bolus of fluid may then be injected through the continuous lumen from the smart torquer to the interventional device, exiting the interventional device into the blood stream from the lumen opening located somewhere along the length of the interventional device. In these instances, a smart torquer may house the necessary electronics to enable temperature measurement from one or more temperature sensors associated with the interventional device. Such temperature sensors may commonly be thermistors, but may also include thermocouples, resistance temperature detectors, integrated circuit temperature sensors, and the like. Also included may be combination pressure sensor/temperature sensor elements, such as temperature-sensitive pressure sensors that are capable of measuring both pressure and temperature. Additionally, in some devices, the interventional device shaft may operate as a temperature sensor (e.g., as a proximal thermistor). Smart torquers in such instance may include appropriate electrical contacts/connections for conductors passing from a distal temperature sensor through the device shaft to the smart torquer, allowing for electrical signals to pass between the sensor and smart torquer circuitry. In such instances, tmart torquers may contain all other necessary electronics for wireless use of such interventional thermodilution devices, such as an A/D converter, microcontroller, wireless communications module, power source, etc. Examples of thermodilution measurement devices that may be configured to be employed with smart torquers of the invention include, but are not limited to: PressureWire Certus/Aeris thermodilution device (St. Jude Medical), Swan-Ganz Catheter thermodilution device (Edwards Lifesciences), etc.

Another type of device with which smart torquers of the invention may be employed is a doppler ultrasound flow measurement device. Such devices may be configured as guidewires and catheters, and are designed to perform blood flow velocity measurements utilizing Doppler ultrasound technology. These devices may include a distal ultrasound transducer, such as those composed of piezoelectric crystals, that both transmit and receive ultrasound waves. For use with such devices, a smart torquer may include the necessary electronics to allow an ultrasound transducer located on an interventional device (such as at the distal tip) to function such that Doppler-based measurements may be obtained. Ultrasound transducers used for Doppler flow velocity measurements are typically composed of piezoelectric crystals. For use with such devices, a smart torquer may house the necessary electronics for supplying a proper voltage/electric field to the piezoelectric transducer such that the transducer converts the electrical stimulation into mechanical energy and generates sound waves at ultrasonic frequencies. Likewise, the Smart Torquer may include the necessary electronics for receiving electrical signals resulting from the reflection of ultrasound waves back to the piezoelectric transducer, where mechanical energy is converted to electrical energy. A smart torquer may house the necessary electronic circuitry, such as specific signal processing circuitry, associated with Doppler ultrasound technology. A smart torquer may house appropriate electrical contacts/connections for conductors passing from a distal transducer through the device shaft to the smart torquer, allowing for electrical signals to pass between the transducer and tmart torquer circuitry. A smart torquer may contain all other necessary electronics for wireless blood flow velocity measurement using Doppler ultrasound, such as an A/D converter, microcontroller, wireless communications module, power source, etc. Examples of a doppler ultrasound devices that may be configured to be employed with smart torquers of the invention include, but are not limited to: the FloWire doppler ultrasound device (Volcano), etc.

Another type of device with which smart torquers of the invention may be employed is a cardiac pressure-volume loop measurement device. Such devices may be configured as guidewires and catheters, and are designed to obtain simultaneous blood pressure and blood volume measurements within a cardiac chamber for the purpose of monitoring and analyzing cardiac function. This is commonly performed using a plot of pressure versus volume, referred to as a pressure-volume loop or pressure-volume diagram, across one or more cardiac cycles. These interventional devices typically contain a distal pressure transducer, such as a solid-state pressure sensor, for pressure measurement, in addition to a set of distal excitation and sensing electrodes for volume measurement. Volume may be obtained using either a traditional conductance technique (Baan's equation) or an admittance technique (Wei's equation). For use with such devices, a smart torquer may house the necessary electronics to enable a pressure sensor, excitation electrodes, and sensing electrodes located on an interventional device to function, allowing for simultaneous measurement of blood pressure and blood volume. For example, a tmart torquer may house the necessary electronics and components to enable the pressure transducer to function, such as excitation voltage circuitry, Wheatstone bridge circuitry, etc. for a piezoresistive sensor, etc., such as described above. In certain pressure-volume loop devices, a pair of excitation electrodes and two or more sensing electrodes are located at the distal end for determining blood conductance in a cardiac chamber, which is then converted to volume data. For use with such devices, a smart torquer may include the necessary electronics for supplying a proper electric current between the excitation electrode, such as a fixed-frequency oscillator (e.g., 20 kHz) that generates a constant-amplitude sine-wave AC current (e.g., 20 µA rms). A smart torquer may house the necessary electronics for receiving and processing electrical signals from the distal sensing electrodes, which are designed to measure voltage that is proportional to the electric field generated between the excitation electrodes, such as electronics configured to receive, amplify, rectify, filter, and invert electrical signals from the sensing electrodes. A smart torquer may house appropriate electrical contacts/connections for conductors passing from distal sensors/electrodes through the device shaft to the smart torquer, allowing for electrical signals to pass between the sensors/electrodes and tmart torquer circuitry. The smart torquer may contain all other necessary electronics for wireless use of such pressure-volume devices, such as an A/D converter, microcontroller, wireless communications module, power source, etc. Examples of a cardiac pressure-volume loop measurement devices that may be configured to be employed with smart torquers of the invention include, but are not limited to: the MPVS Ultra/Ventri-Cath cardiac pressure-volume loop measure device (Millar); the Scisense ADV500 cardiac pressure-volume loop measurement device (Transonic Systems), etc.

Another type of device with which smart torquers of the invention may be employed is intravascular ultrasound (IVUS) imaging device. For such devices, a smart torquer may include the necessary electronic components to allow one or more ultrasound transducers located on an interventional device (such as at the distal tip) to operate so that ultrasound images may be obtained wirelessly. Related to IVUS, imaging devices may include an array, such as a phased array, of circumferentially arranged ultrasound transducers mounted at the distal tip of the device. These ultrasound transducers may be made up of piezoelectric crystals. For use with such devices, a smart torquer may house the necessary electronics for supplying the proper voltage/electric field to the piezoelectric transducers such that the transducers generate sound waves at ultrasonic frequencies. Likewise, a smart torquer may house the necessary electronics for receiving electrical signals resulting from the reflection of ultrasound waves back to the piezoelectric transducers. As an alternative to an array of piezoelectric transducers, an IVUS device may include an array of capacitive micromachined ultrasonic transducers (CMUT) to enable imaging via capacitive changes and membrane deflection/vibration. The CMUT array may be integrated with front-end electronics in a single-chip layout. For use with such devices, a smart torquer may house the necessary electronics to allow a CMUT array to both generate and receive ultrasound waves. For example, a smart torquer may include electronics for supplying a DC bias voltage and an AC voltage across capacitor terminals to induce membrane vibration and generation of ultrasound waves. The smart torquer electronics may communicate directly with the CMUT array and/or directly with the front-end electronics integrated with the CMUT array. In such instances, a tmart torquer may house the necessary electronic circuitry, such as specific signal processing circuitry, associated with ultrasound imaging technology. A smart torquer may include appropriate electrical contacts/connections for conductors passing from distal transducers through the device shaft to the smart torquer, allowing for electrical signals to pass between the transducers and smart torquer circuitry. In such instances, smart torquers may contain all other necessary electronics for wireless IVUS imaging, such as an A/D converter, microcontroller, wireless communications module, power source, etc. Examples of a IVUS devices that may be configured to be employed with smart torquers of the invention include, but are not limited to: the s5 Imaging System IVUS device, the Eagle Eye Catheter IVUS device and the Visions PV Catheter IVUS device (Volcano); and the iLab Ultrasound Imaging System IVUS device (Boston Scientific); etc.

Another type of device with which smart torquers of the invention may be employed is an electrophysiology device. Such devices may be configured as guidewires and catheters, and are used for cardiac EP studies, electroanatomical mapping prior to ablation, etc., which may be converted to a wireless format by a smart torquer of the invention. Such devices include loop catheters for cardiac EP mapping, basket catheters for cardiac EP mapping, diagnostic catheters for recording intracardiac electric potentials and/or providing pacing stimuli, and the like. For use with such devices, a smart torquer may include the necessary electronics to enable interventional EP devices to measure electrical activity, such as cardiac electrical activity, and to deliver electrical stimuli, such as cardiac pacing stimuli. EP devices may include two or more electrodes positioned at the distal region of the device (e.g., at the distal tip and/or along the distal portion of the shaft). The electrodes may be used to record electrical activity, to deliver electrical stimuli, or both. Such electrodes may be connected to a conductor, such as a wire, that passes from the electrode and through the interventional device shaft to the proximal handle/connector of the device. The proximal handle/connector may then interface to an external unit containing electronics for signal processing, display, etc. For use with such devices, a smart torquer interfaced may include appropriate electrical contacts/connections for conductors passing from distal electrodes through the EP device shaft to the smart torquer, allowing for electrical signals to pass between the electrodes and smart torquer circuitry. In such instances, smart torquers may house the necessary electronic circuitry, such as specific signal processing circuitry, associated with acquisition of electrophysiological signals (e.g., intracardiac electric potentials), electroanatomical mapping, etc. A smart torquer may house the appropriate electronics, such as pulse generator circuitry, for delivering electrical energy (e.g., a cardiac pacing stimulus) to the patient via the electrodes. In such instances, a smart torquer may contain all other necessary electronics for wireless use of EP devices, such as an A/D converter, microcontroller, wireless communications module, power source, etc. Examples of a electrophysiology devices that may be configured to be employed with smart torquers of the invention include, but are not limited to: the Blazer Dx-20 Steerable Diagnostic Catheter electrophysiology device (Boston Scientific); the Topera/FIRMap electrophysiology device (Abbott); the Constellation and Rhythmia electrophysiology devices (Boston Scientific); the CARTO PENTARAY electrophysiology device, Biosense Webster); the Achieve Mapping Catheter electrophysiology device (Medtronic); the Pacel Bipolar Pacing Catheter electrophysiology device (St. Jude Medical); etc.

Another type of device with which smart torquers of the invention may be employed is a multiplex device. Such devices may be configured as guidewires and catheters, and include more than one type of sensor, such that more than one type of physiologic measurement may be obtained from a single interventional device. In some examples, multiple types of measurements may be combined (i.e., mathematically related) to derive a new measurement. Examples of such devices include, but are not limited to: pressure and doppler flow devices, pressure and thermodilution flow devices, etc. For use with such devices, a smart torquer may include the necessary electronics and components to enable operation of multiple types of sensors belonging to a single interventional device, allowing for more than one type of physiologic measurement to be obtained from the interventional device while incorporating wireless functionality.

Another type of device with which smart torquers of the invention may be employed is a steerable, deflectable and/or expandable device. Such devices may be configured as guidewires and catheters, and have a distal end that can be deflected in one or more directions via actuation of a steering mechanism, which may be located at the proximal end of the device (e.g., integrated with the device handle). Alternatively or in addition to, such devices may include a component, such as a sensing component, at the distal end that can be expanded/retracted via actuation of a mechanism located at the proximal end of the device. For use with such devices, a smart torquer may include the necessary internal and external mechanisms to enable controlled deflection of a steerable interventional device tip while the smart torquer is connected to the interventional device. Likewise, the smart torquer may include the necessary internal and external mechanisms to enable controlled expansion/retraction of distal components built into the interventional device. A steerable interventional device may have a distal end that can be deflected to aid in navigation through the cardiovascular system. Deflection may be unidirectional (one-way deflectable), bidirectional (two-way deflectable), or multi-directional (4-way deflectable). Many electrophysiology catheters having electrodes at the distal end for electrical sensing and/or electrical stimulation are deflectable at the distal end. For the mechanism of deflection, such steerable devices may employ one or more internal pull wires that are anchored at the distal end of the device (e.g., anchored to a pull ring) and pass through a lumen or lumens in the shaft to the proximal end of the device, where they join directly or via any internal mechanisms to an external steering mechanism. The external steering mechanism, which allows the operator to deflect the tip, may be a wheel, a knob, a thumb control, a sliding handle, a rotating handle, etc. For use with such devices, a smart torquer may include a user-controlled external steering mechanism and any necessary internal mechanisms, such that the mechanisms are compatible with the deflection mechanisms in the interventional device when the smart torquer is connected to the device. In such instances, a smart torquer may be used to deflect a steerable interventional device tip while also providing the necessary electronics/components for sensor functionality and wireless data transmission. In such instances, a smart torquer may include any convenient technology for enabling sensor functionality in addition to steerability, such as described above. For example, with respect to deflectable electrophysiology devices, a smart torquer may include the necessary electronics to enable interventional EP devices to measure electrical activity, such as cardiac electrical activity, and to deliver electrical stimuli, such as cardiac pacing stimuli, e.g., as described above.

Some interventional sensing devices may have expandable/retractable distal components. For example, basket catheters for cardiac EP mapping may consist of a distal basket structure, often composed of multiple splines, that can be expanded and retracted by the operator via actuation of a mechanism located at the proximal end of the device (e.g., at the handle of the device). The user-controlled mechanism for expanding (i.e., deploying) and retracting the basket structure may be one of many embodiments, such as a sliding handle, a rotating handle, etc. For use with such devices, a smart torquer may include a user-controlled external mechanism and any necessary internal mechanisms, such that the mechanisms are compatible with the expansion/retraction mechanisms in the interventional device when the smart torquer is connected to the device. Therefore, the smart torquer may be used to expand/retract interventional device components, such as a distal basket structure on an EP mapping catheter, while also providing the necessary electronics/components for sensor functionality and wireless data transmission. A smart torquer may include any convenient components for enabling sensor functionality in addition to expansion/retraction of distal components, e.g., as described above. For example, with respect to basket EP mapping catheters, which typically consist of multiple electrodes located along the splines of the basket structure, a smart torquer may include the necessary electronics to enable measurement of electrical activity and electroanatomical mapping, e.g., as described above. In such instances, a smart torquer may include the necessary mechanisms to enable both tip deflection (i.e., steering) and expansion/retraction of distal components in a single interventional device by combining the concepts previously described.

Another type of device with which smart torquers of the invention may be employed is a needle-based device. Such devices may be configured to access specific regions within the body, such as the intravascular space (e.g., arteries and veins) and the pericardial space. These devices may be equipped with sensors, such as pressure sensors, for physiologic measurements. Use of the Smart Torquer with these devices allows for wireless transmission of physiologic data and enhanced manipulation/handling when performing needle-based access. These devices may include a rigid needle for percutaneous entry into specific structures/compartments of the body. The needle may contain one or more sensors for obtaining physiologic information. A particular example is a needle-based device designed for entry into the pericardial cavity, typically via a subxiphoid approach, to enable subsequent entry into the cavity by interventional electrophysiology devices, which then have access to the epicardial surface of the heart; epicardial EP procedures can then be performed. The needle-based device may be equipped with a pressure sensor at the distal tip of the needle, such that pressure data can be displayed and analyzed during access. Pressure waveforms specific to the pericardial cavity can be identified, confirming that the needle has correctly entered the pericardial cavity. In a preferred embodiment, the pressure sensor is a fiber optic pressure sensor. For use with such devices, a smart torquer may include the necessary electronic, electro-optical, and optical elements to allow an optical pressure sensor located on the access needle to operate while maintaining wireless functionality, e.g., as described above. Alternatively, the pressure sensor may be any of several types and configurations, including a distal solid-state pressure sensor, a fluid-filled configuration, etc. The smart torquer may include the necessary electronics and components to enable such pressure sensors to function, e.g., as described above. Needle-based sensing devices may include other types of sensors for various measurements and applications. In such instances, a smart torquer may be configured to facilitate functionality of such sensors. The needles may be hollow (i.e., consisting of a hollow lumen). For such devices, a smart torquer may contain a hollow lumen that aligns and interfaces/joins with the corresponding lumen contained in the needle when the smart torquer is connected to the needle, such that the lumens are in communication, effectively forming one continuous lumen extending throughout and allowing the lumen to be used for its purpose while leaving the smart torquer connected to the needle. In such instances, a smart torquer may contain all other necessary electronics for enabling wireless functionality of needle-based sensing devices, such as an A/D converter, microcontroller, wireless communications module, power source, etc. A smart torquer may be designed to aid manual control/navigation of the needle, as desired. Examples of a needle based devices that may be configured to be employed with smart torquers of the invention include, but are not limited to: the EpiAccess System needle device (EpiEP); the SmartNeedle needle device (Vascular Solution); etc.

Kits

Aspects of the invention further include kits that include one or more smart torquers of the invention, e.g., as described above. Such kits at least include a smart torquer, e.g., as described above. The kits may include one or more additional components that may find use in a given protocol, such as an elongated intravascular device, such as described above. In some instances, the elongated intravascular device and smart torquer may be connected, e.g., operably engaged, in the kit. The smart torquer (and other components when present) of the kits may be present in a suitable container, such as a sterile container, e.g., a sterile pouch. Where more than one component is present, the components may be present in individual containers or at least some of the components may be combined in a single container.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another form of these instructions is a computer readable medium, e.g., diskette, compact disk (CD), Hard Drive etc., on which the information has been recorded. Yet another form of these instructions that may be present is a website address which may be used via the internet to access the information at a removed site.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:
1. A method comprising:
introducing a proximal end of an elongated intravascular device into an engager of a torquer comprising:
(a) the engager for releasably engaging the elongated intravascular device;
(b) a communications module;
(c) a first set of contacts associated with the engager and configured to communicatively contact the elongated intravascular device engaged by the engager with the communications module; and (d) a manipulator configured to allow a user to torque the elongated intravascular device engaged by the engager; and determining a contact configuration between the first set of contacts of the torquer and a second set of contacts of the elongated intravascular device, wherein determining the contact configuration is based at least in part on monitoring impedance between each contact in the first set of contacts and a contact switch network of the torquer.

2. The method according to claim 1, wherein the method further comprises introducing a distal end of the elongated intravascular device into vasculature of a patient.

3. The method according to claim 2, wherein the distal end of the elongated intravascular device is introduced into the vasculature of the patient prior to introducing the proximal end of the elongated intravascular device into the engager.

4. The method according to claim 1, wherein the engager is coupled to the intravascular device prior to removal of the intravascular device from sterile packaging.

5. The method according to claim 1, wherein the engager comprises a constrictor and the method further comprises constricting the constrictor about a region of the elongated intravascular device that is present in the engager.

6. The method according to claim 1, wherein the method further comprising torqueing the elongate intravascular device by manipulating the manipulator.

7. The method according to claim 1, wherein the method further comprises transmitting a signal from the communications module to a second device.

8. The method according to claim 1, wherein the elongated intravascular device comprises a catheter or a guidewire.

9. The method according to claim 8, wherein the guidewire comprises:

(a) an elongated conductor comprising:

(i) an elongated structure having a proximal region and a distal region and comprising two or more insulated conducting members that are in fixed relative position along at least a portion of the elongated structure and extend from the proximal region to the distal region; and (ii) a pattern of insulation openings among the insulated conducting members at one or both of the proximal and distal regions;

(b) a connector positioned at the proximal region of the elongated structure; and (c) an effector positioned at the distal region of the elongated structure.

10. The method according to claim 1, wherein the engager further comprises a seal for fluidically sealing the proximal end of the elongated intravascular device inside of the torquer.

11. The method according to claim 1, wherein the first set of contacts is configured to provide electrical communication between the elongated intravascular device and the communications module.

12. The method according to claim 1, wherein each contact in the first set of contacts comprises an electrode.

13. The method according to claim 1, wherein at least one contact in the first set of contacts comprises a ring electrode.

14. The method according to claim 1, wherein the communications module comprises circuitry.

15. The method according to claim 1, wherein the torquer further comprises a power source.

16. The method according to claim 15, wherein the power source comprises a battery.

17. The method according to claim 1, wherein the torquer comprises an attachment component.

18. The method according to claim 1, wherein at least a portion of the elongated intravascular device is configured to one-time use.

19. The method according to claim 2, wherein the patient is a mammal.

20. The method according to claim 19, wherein the mammal is a human.

21. The method according to claim 14, further comprising coupling the circuitry with corresponding ones of contacts of the second set of contacts of the elongated intravascular device based on which one of contacts in the first set of contacts of the torquer register as being electrically connected based at least in part on the monitored impedance.

* * * * *